(12) United States Patent
Manners et al.

(10) Patent No.: US 6,909,032 B2
(45) Date of Patent: Jun. 21, 2005

(54) DNA ENCODING A MACADAMIA INTEGRIFOLIA ANTI-MICROBIAL PROTEIN, CONSTRUCTS COMPRISING THE SAME AND PLANT MATERIAL COMPRISING THE CONSTRUCTS

(75) Inventors: John Michael Manners, Paddington (AU); John Paul Marcus, Grand Rapids, MI (US); Kenneth Clifford Goulter, Jamboree Heights (AU); Jodie Lyn Green, Toowong (AU); Stuart John Harrison, Norwich (GB)

(73) Assignees: Commonwealth Scientific and Industrial Research Organisation, Campbell (AU); The State of Queensland, Department of Primary Industries, Brisbane (AU); The University of Queensland, St, Lucia (AU); Bureau of Sugar Experiments Stations, Indooroopilly (AU); Queensland University of Technology, Brisbane (AU)

( * ) Notice: Subject to any disclaimer, the term of this patent is extended or adjusted under 35 U.S.C. 154(b) by 0 days.

(21) Appl. No.: 09/882,434

(22) Filed: Jun. 15, 2001

(65) Prior Publication Data

US 2002/0108144 A1 Aug. 8, 2002

Related U.S. Application Data

(63) Continuation of application No. 09/364,395, filed on Jul. 30, 1999, now abandoned, which is a continuation-in-part of application No. 09/117,615, filed as application No. PCT/AU97/00052 on Jan. 31, 1997, now abandoned.

(30) Foreign Application Priority Data

Jan. 31, 1996 (AU) ............................................ PN7802

(51) Int. Cl.$^7$ ........................... A01H 5/00; C12N 15/82; C12N 15/31
(52) U.S. Cl. ........................ 800/301; 435/418; 536/300
(58) Field of Search .............................. 800/301, 279, 800/322, 320, 320.1, 306, 317.4, 312, 317.3, 314, 320.3, 317.2, 319, 323, 3, 320.2; 424/93.2; 435/418, 419, 348, 252.3, 520.1

(56) References Cited

U.S. PATENT DOCUMENTS 5,919,918 A  7/1999  Broekaert et al.

FOREIGN PATENT DOCUMENTS

WO   WO 92/21699   12/1992
WO   WO 97/28185   * 8/1997

OTHER PUBLICATIONS

Lazar et al, 1988, Mol. Cell. Biol. 8:1247–1252.*
Hill et al, 1998, Biochem. Biophys. Res. Comm. 244:573–577.*
McManus et al, 1999, J. Mol. Biol. 293:629–639.*
Terras et al, 1995, Plant Cell 7:573–588.*
Gordon–Kamm et al, 1990, Plant Cell 2:603–618.*
Koziel et al., *Optimizing expression of transgenes with an emphasis on post–transcriptional events, Plant Molecular Biology*, vol. 32, 1996, pp. 393–405.
Stam et al., *The Silence of Genes in Transgenic Plants, Annals of Botany*, vol. 79, 1997, pp. 3–12.
Smith, C.J.S., et al., *Antisense RNA inhibition of polygalacturonase gene expression in transgenic tomatoes, Letters to Nature*, vol. 334, Aug. 25, 1998, pp. 724–726.
De Bolle, M. et al., *Mirabilis Jalapa Antibacterial Peptides and Raphanus Sativus Antifungal Proteins: A Comparative Study of Their Structure and Biological Activities, Mechanisms of Plant Defense*, 1993, pp. 433–436.
Byler et al., *Neotropical Natural Products: Antimicrobial Activity of Essential Oils of Flora From Monteverde, Costa Rica, The Journal of the Alabama Academy of Science*, vol. 62, No. 2–3, Apr.–Jul. 1991, pp. 86–87.
Jacob et al., *Potential therapeutic applications of magainins and other antimicrobial agents of animal origin, Antimicrobial Peptides*, 1994, pp. 197–223.

* cited by examiner

Primary Examiner—Anne Kubelik
(74) Attorney, Agent, or Firm—Knobbe Martens Olson and Bear, LLP

(57) ABSTRACT

The subject invention relates to DNA encoding an antimicrobial protein from *Macadamia integrifolia* and variants of the protein that are less sensitive to $Ca^{++}$. The invention further relates to constructs comprising the DNA, and host cells, plants and plant material comprising such constructs.

13 Claims, 10 Drawing Sheets

```
ATTAAGTCTTTGAGTCTCATATACATACTCTTTCTCCTCCCCACCATT      45
AGCACTTATCAGCTAACCCTCAGCCATGGCCTTCCACCAAGTTGTTC       90
                     M  A  S  T  K  L  F
TTCTCTGTCATTACTGTGATGCTCATAGCAATGGCAAGTGAG           135
 F  S  V  I  T  V  M  L  I  A  M  A  S  E
ATGGTGAATGGGAGTGCATTTACAGTATGGAGTGGTCCAGGTTGT        180
 M  V  N  G  S  A  F  T  V  W  S  G  P  G  C
AACAACCGTGCTGAGCGATATAGCAAGTGTGGATGCTCAGCTATA        225
 N  N  R  A  E  R  Y  S  K  C  G  C  S  A  I
CATCAGAAGGGAGGCTATGACTTCAGCTACACTGGACAAACTGCT        270
 H  Q  K  G  G  Y  D  F  S  Y  T  G  Q  T  A
GCTCTCTACAACCAGGATGCCAGTGGATGCAGTGGTTGCACACCAGG      315
 A  L  Y  N  Q  D  A  S  G  C  S  G  V  A  H  R
TTTGGGTCCAGTGCCAGGGCATGCAACCCTTTTGGTTGGAAGAGT        360
 F  G  S  S  A  R  A  C  N  P  F  G  W  K  S
ATCTTCATCCAATGCTAGATTTCATAACTCTTGGATCCATCTTCT        405
 I  F  I  Q
ATGTTTTTCAAGTGTATAATTAGAGAGATGCATGGATATATAATA        450
AATAAGTAAAAGCTACCGGTATCACCATGTGATGATTTTYACCC         493
```

Fig. 6

Amplification 1
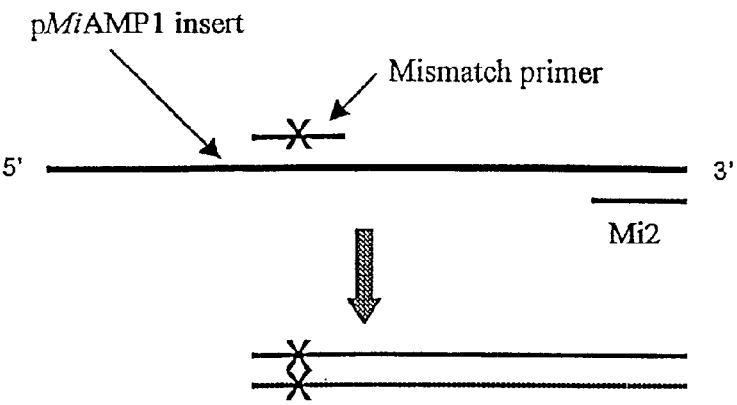
Amplification 2
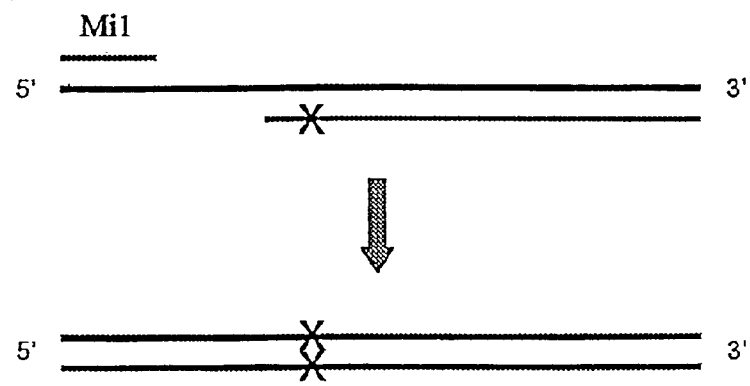
Amplification 3
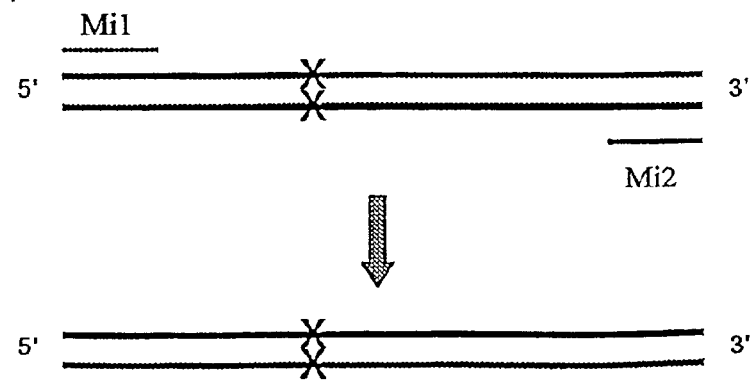
Fig. 11

DNA ENCODING A MACADAMIA INTEGRIFOLIA ANTI-MICROBIAL PROTEIN, CONSTRUCTS COMPRISING THE SAME AND PLANT MATERIAL COMPRISING THE CONSTRUCTS

CROSS-REFERENCE TO RELATED APPLICATIONS

This application is a continuation of U.S. application Ser. No. 09/364,395, filed Jul. 30, 1999, now abandoned which is a continuation-in-part of U.S. application Ser. No. 09/117,615 filed Nov. 9, 1998, now abandoned, which is the U.S. national phase under 35 U.S.C. § 371 of International Application No. PCT/AU97/00052, filed Jan. 31, 1997.

TECHNICAL FIELD

This invention relates to isolated proteins that exert inhibitory activity on the growth of fungi and bacteria, which fungi and bacteria include some microbial pathogens of plants and animals. The invention also relates to recombinant genes which include sequences encoding the anti-microbial proteins, the expression products of which can contribute to the plant cell's or another organism's cell's defense against invasion by microbial pathogens. The invention further relates to the use of the proteins and/or genes encoding the proteins for the control of microbes in human and veterinary clinical conditions.

BACKGROUND ART

Microbial diseases of plants are a significant problem to the agricultural and horticultural industries. Plant diseases in general annually cause millions of tonnes of crop losses with fungal and bacterial diseases responsible for significant portions of these losses. One possible way of combating fungal and bacterial diseases is to provide transgenic plants capable of expressing a protein or proteins that in some way increase the resistance of the plant to pathogen attack. A simple strategy is to first identify a protein with anti-microbial activity in vitro, to clone the DNA sequence encoding the protein, to make a chimeric gene construct for efficient expression of the protein in plants, to transfer this gene to transgenic plants and to assess the effect of the introduced gene on resistance to microbial pathogens by comparison with control plants.

The first and most important step in the strategy for disease control described above is to identify a protein with strong anti-microbial activity. In recent years, many different plant proteins with anti-microbial and/or antifungal activity have been identified and described. These proteins have been categorized into several classes according to either their presumed mode of action and/or their amino acid sequence homologies. These classes include the following: chitinases (Roberts, W. K. et al. [1986] *Biochim. Biophys. Acta* 880:161–170); β-1,3-glucanases (Manners, J. D. et al. [1973] *Phytochemistry* 12:547–553); thionins (Bolmann, H. et al. [1988] *EMBO J.* 7:1559–1565 and Fernadez de Caleya, R. et al. [1972] *Appl. Microbiol.* 23:998–1000); permatins (Roberts, W. K. et al. [1990] *J. Gen. Microbiol.* 136:1771–1778 and Vigers, A. J. et al. [1991] *Mol. Plant-Microbe Interact.* 4:315–323); ribosome-inactivating proteins (Roberts, W. K. et al. [1986] *Biochim. Biophys. Acta* 880:161–170 and Leah, R. et al. [1991] *J. Biol. Chem.* 266:1564–1573); plant defensins (Terras, F. R. G. et al. [1995] *The Plant Cell* 7:573–588); chitin binding proteins (De Bolle, M. F. C. et al. [1992] *Plant Mol. Biol.* 22:1187–1190 and Van Parijs, J. et al. [1991] *Planta* 183:258–264); thaumatin-like, or osmotin-like proteins (Woloshuk, C. P. et al. [1991] *The Plant Cell* 3:619–628 and Hejgaard, J. [1991] *FEBS Letts.* 291:127–131); PR1-type proteins (Niderman, T. et al. [1995] *Plant Physiol.* 108:17–27); the non-specific lipid transfer proteins (Terras, F. R. G. et al. [1992] *Plant Physiol.* 100:1055–1058 and Molina, A. et al. [1993] *FEBS Letts.* 3166:119–122); and, the knottin or knottin-like proteins (Cammue, B. P. A. et al. [1992] *J. Biol. Chem.* 67:2228–2233). In addition, plants are not the sole source of anti-microbial proteins and there are many reports of the isolation of anti-microbial proteins from animal and microbial cells (reviewed in Gabay, J. E. [1994] *Science* 264:373–374 and in "Anti-microbial peptides" [1994] *CIBA Foundation Symposium* 186, John Wiley and Sons Publ., Chichester, UK).

There is some evidence that the ectopic expression of genes encoding proteins that have in vitro anti-microbial activity in transgenic plants can result in increased resistance to microbial pathogens. Examples of this engineered resistance include transgenic plants expressing genes encoding: a plant chitinase, either alone (Broglie, K. et al. [1991] *Science* 254:1194–1197) or in combination with a β-1,3-glucanase (Van den Elzen, P. J. M. et al. [1993] *Phil. Trans. Roy. Soc.* 342:271–278); a plant defensin (Terras, F. R. G. et al. [1995] *The Plant Cell* 7:573–588); an osmotin-like protein (Liu, D. et al. [1994] *Proc. Natl. Acad. Sci. USA* 91:1888–1892); a PR1-class protein (Alexander, D. et al. [1993] *Proc. Natl. Acad. Sci. USA* 90:7327–7331) and a ribosome-inactivating protein (Logemann, J. et al. [1992] *Bio/Technology* 10:305–308).

Although the potential use of anti-microbial proteins for engineering disease resistance in transgenic plants has been described extensively, there are other applications which are worthy of mention. Firstly, highly potent anti-microbial proteins can be used for the control of plant disease by direct application (De Bolle, M. F. C. et al. [1993] in *Mechanisms of Plant Defence Responses*, B. Fritig and M. Legrand eds., Kluwer Acad. Publ., Dordrecht, NL, pp. 433–436). In addition, anti-microbial peptides have potential therapeutic applications in human and veterinary medicine. Although this has not been described for peptides of plant origin it is being actively explored with peptides from animals and has reached clinical trials (Jacob, L. and Zasloff, M. [1994] in "Anti-microbial Peptides", *CIBA Foundation Symposium* 186, John Wiley and Sons Publ., Chichester, UK, pp. 197–223).

The invention described herein constitutes a previously undiscovered and novel protein with anti-microbial activity. This protein can be isolated from *Macadamia integrifolia* (*Mi*) plants. *Macadamia integrifolia* belongs to the family Proteaceae. *M. integrifolia*, also known as Bauple Nut or Queensland Nut, is considered by some to be the world's best edible nut. For this reason it is extensively cultivated commercially, both in Australia and overseas (Williams, Keith A. W., *Native Plants (Queensland)*, Volume II, 1984, published by Keith A. W. Williams and printed by Printcraft of Newstead, Qld, Australia).

An object of the invention is to provide a protein having anti-microbial activity, homologues of the protein, and variants of the protein.

A further object of the invention is to provide DNA encoding anti-microbial protein, homologues of the proteins and variants of the protein.

Yet another object of the invention is to provide DNA constructs which include DNA encoding anti-microbial protein, homologues of the protein and variants of the protein.

Still further objects of the invention are to provide cells and plants harbouring a DNA construct which includes DNA encoding anti-microbial protein, homologues of the protein and variants of the protein, and to provide reproductive tissue of said plant.

Additional objects of the invention are to provide compositions comprising the anti-microbial protein, homologues and variants, and methods of treating plants and humans for microbial infestation using the proteins and compositions according to the invention.

SUMMARY OF THE INVENTION

According to a first embodiment of the invention, there is provided an isolated or synthetic anti-microbial protein selected from the group consisting of:

(i) a protein which includes an amino acid sequence corresponding to residues 27 to 102 of the sequence shown in FIG. 6 (SEQ ID NO: 1);

(ii) a homologue of (i);

(iii) a variant of (i); and (iv) a protein isolated from the family Proteaceae which specifically reacts with antibodies raised against (i) and which has essentially the same anti-microbial activity as (i).

According to a second embodiment of the invention, there is provided an isolated or synthetic DNA which encodes a protein according to the first embodiment.

According to a third embodiment of the invention, there is provided a DNA construct which includes a DNA according to the second embodiment operatively linked to elements for the expression of said encoded protein.

According to a fourth embodiment of the invention, there is provided a host cell harbouring a DNA construct according to the third embodiment.

According to a fifth embodiment of the invention, there is provided a transgenic plant harbouring a DNA construct according to the third embodiment.

According to a sixth embodiment of the invention, there is provided reproductive material of a transgenic plant according to the fifth embodiment.

According to a seventh embodiment of the invention, there is provided a composition comprising an anti-microbial protein according to the first embodiment together with an agriculturally acceptable carrier, diluent or excipient.

According to an eighth embodiment of the invention, there is provided a composition comprising an anti-microbial protein according to the first embodiment together with a pharmaceutically acceptable carrier, diluent or excipient.

According to a ninth embodiment of the invention, there is provided a method of controlling microbial infestation of a plant, the method comprising:

i) introducing a DNA construct according to the third embodiment into said plant; or ii) treating said plant with an anti-microbial protein according to the first embodiment or a composition according to the seventh embodiment.

According to a tenth embodiment of the invention, there is provided a method of controlling microbial infestation of a mammalian animal, the method comprising treating the animal with an anti-microbial protein according to the first embodiment or a composition according to the eighth embodiment.

Other embodiments of the invention include methods for producing anti-microbial protein and variants thereof.

BRIEF DESCRIPTION OF THE DRAWINGS

FIG. 6 shows the amino acid sequence of MiAMP1 (SEQ ID NO: 1) together with a nucleotide sequence (SEQ ID NO: 2) which encodes the protein.

FIG. 11 is a schematic representation of the mutagenesis procedure used to produce variants of MiAMP1.

DETAILED DESCRIPTION OF THE INVENTION

Figure 1:
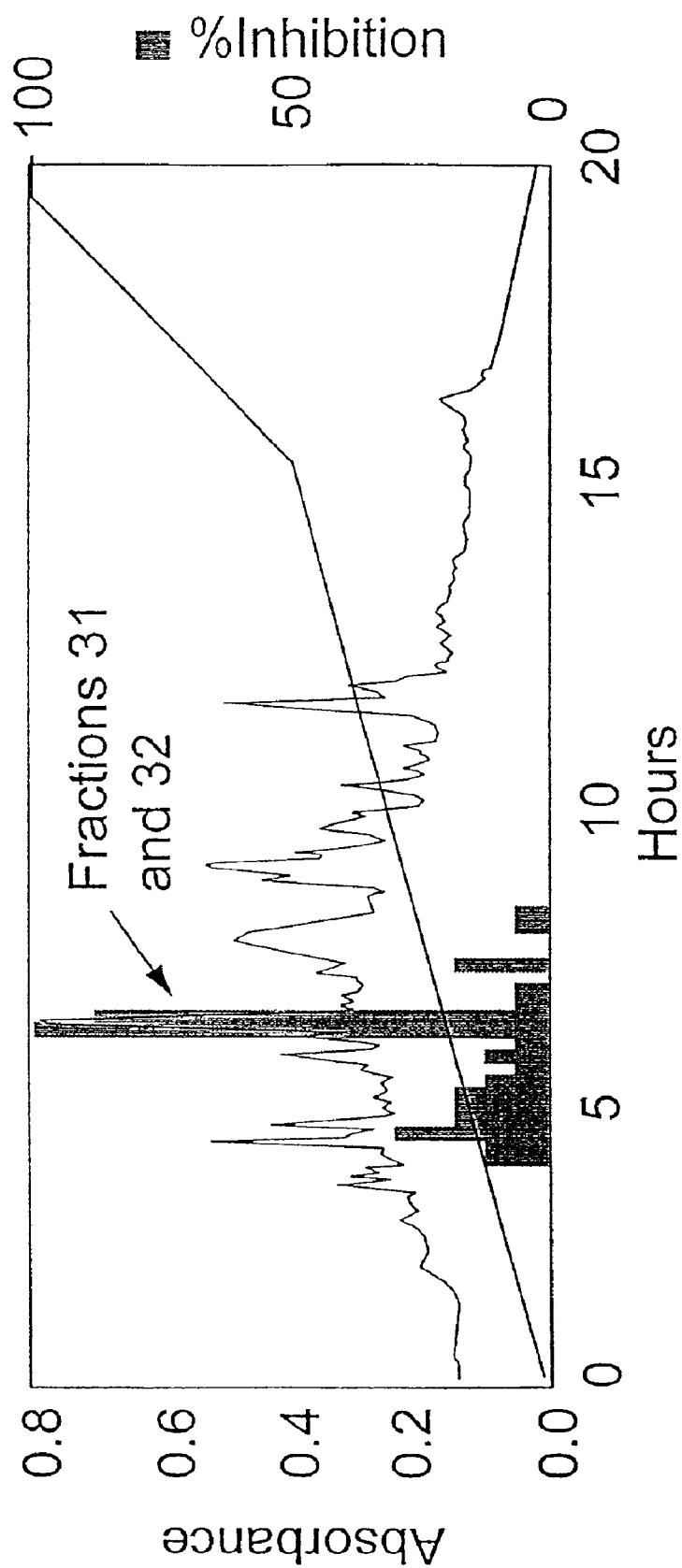
FIG. 1 shows a cation-exchange chromatography profile of the basic protein fraction extracted from *Macadamia* nuts with the results of a bioassay shown for fractions of interest.

| | |
|---|---|
| FBS | foetal bovine serum |
| EDTA | ethylenediaminetetraacetic acid |
| LDH | lactate dehydrogenase |
| MeCN | methyl cyanide (acetonitrile) |
| Mi | *Macadamia integrifolia* |
| MiAMP1 | *Macadamia integrifolia* anti-microbial protein 1NDnot determined |

-continued

| PCR | polymerase chain reaction |
|---|---|
| PMSF | phenylmethylsulphonyl fluoride |
| SDS-PAGE | sodium dodecylsulphate polyacrylamide gel electrophoresis |
| TFA | trifluoroacetic acid |
| TPCK | tosylphenylalanine chloromethylketone |
| RACE | rapid amplification of cDNA ends |

The present inventors have identified a new class of anti-microbial proteins. A prototype protein can be isolated from seeds of *Macadamia integrifolia* (hereafter *Mi*). The invention thus provides an anti-microbial protein per se as well as DNA sequences encoding anti-microbial protein.

The invention also provides a method of obtaining related proteins from plant tissue of the family Proteaceae. With antibodies raised against a particular example of the anti-microbial protein—*Macadamia integrifolia* anti-microbial protein number one (MiAMP1)—it is possible to screen tissue from other species of trees related to *Macadamia integrifolia*. Other species of *Macadamia* as well as species in the broader category of the family Proteaceae are primary targets for such screening. Indeed, as shown in Example 10, such screening has been used to identify several species which contain proteins that are related to MiAMP1 based on antigenic response, size, and localisation in seed tissue. Screening for related proteins need not be restricted to the Proteaceae family as it is likely that other species may also contain similar proteins.

The invention also provides an amino acid sequence of the prototype anti-microbial protein (Example 9). From this sequence, the sequence of DNA encoding the protein can be derived by reverse translating the amino-acid sequence. DNA having a nucleotide sequence encoding anti-microbial protein can then be synthesised chemically (and/or enzymically) or isolated from plant tissue of *Macadamias* using standard cloning methods as described in laboratory manuals such as *Current Protocols in Molecular Biology* (copyright 1987–1995, edited by Ausubel F. M. et al. and published by John Wiley & Sons, Inc., printed in the USA). The entire content of Ausubel et al. is incorporated herein by cross-reference.

The anti-microbial protein per se will manifest a particular three-dimensional structure that can be determined by using x-ray crystallography or nuclear magnetic resonance techniques. This structure will be responsible in large part for the anti-microbial activity of the protein. From the sequence of the protein, it is also possible to make predictions concerning possible conformations and structural motifs (secondary structure) that will likely be exhibited by the protein. It will be appreciated that one skilled in the art can take a protein with known structure and alter the sequence significantly and yet retain the overall three-dimensional shape and anti-microbial activity of the protein. One aspect of the structure that most likely could not be altered without serious consequences is the cysteine content and spacing of the cysteine residues since this would disrupt the formation of disulfide bonds which are critical to maintaining the overall structure of the protein. Other residues which are likely to be critical in determining the shape and function of the protein are glycine and proline which assume unique conformations in the backbones of proteins. As well, the distribution of charged residues (i.e. arginine, lysine, histidine, glutamate, and aspartate) in the three dimensional space of the protein will be important to the structure and the activity which is exhibited. In particular, a high density of positively charged residues has been shown to confer anti-microbial activity in a variety of proteins (Pathak et al. [1995] *PROTEINS: Structure, Function and Genetics* 22:182–186).

DNA sequences coding for these proteins can be deduced using standard codon tables. Using this finite number of possible DNA sequences, suitable oligonucleotide probes can be derived and used to isolate the actual gene(s) (Example 11) as well as control sequences. It is also possible to chemically synthesise the gene using a standard DNA synthesis instrument (such as a Beckman Oligo1000 instrument) together with known techniques for constituting synthesised gene fragments into a whole gene (see *Current Protocols in Molecular Biology*, supra).

This gene, under control of a constitutive or inducible promoter (Examples 12 and 14), can then be cloned into a biological system that allows expression of the protein (Examples 13 and 15). Transformation methods allowing for the protein to be expressed in a variety of systems are known. The protein can thus be expressed in any suitable system for the purpose of producing the protein for further use. Suitable hosts for the expression of this protein include *E. coli*, fungal cells, insect cells, mammalian cells, and plants. Standard methods for expressing proteins in such hosts are described in a variety of texts including section 16 (Protein Expression) of *Current Protocols in Molecular Biology* (supra).

Plant cells can be transformed with DNA constructs of the invention according to a variety of known methods (*Agrobacterium*, Ti plasmids, electroporation, micro-injections, micro-projectile gun, and the like). For expression in plants, the DNA sequence encoding MiAMP1, for example, can be used in conjunction with a DNA sequence encoding the native or a heterologous signal peptide sequence which will target the protein to a particular cell compartment (e.g., the apoplast or the vacuole). These coding sequences can be ligated to a plant promoter sequence that will ensure strong expression in plant cells. This promoter sequence may ensure strong constitutive expression of the protein in most or all plant cells, it may be a promoter which ensures expression in specific tissues or cells that are susceptible to microbial infection and it may also be a promoter which ensures strong induction of expression during the infection process. These types of gene cassettes will also include a transcription termination and polyadenylation sequence 3' of the MiAMP coding region to ensure efficient production and stabilisation of the mRNA encoding the MiAMP. It is possible that efficient expression of the MiAMP might be facilitated by inclusion of its DNA sequence into a sequence encoding a much larger protein which is processed in planta to produce one or more active MiAMP molecules. Gene cassettes encoding MiAMP as described above can then be expressed in plant cells using two common methods. Firstly, the gene cassettes could be ligated into binary vectors carrying, i) left and right border sequences that flank the T-DNA of the *Agrobacterium tume-* faciens Ti plasmid, ii) a suitable selectable marker gene for the selection of antibiotic resistant plant cells, iii) origins of replication that function in either *A. tumefaciens* or *Escherichia coli* and iv) antibiotic resistance genes that allow selection of plasmid-carrying cells of *A. tumefaciens* and *E. coli*. This binary vector carrying the chimeric MiAMP1 encoding gene could be introduced by either electroporation or triparental mating into *A. tumefaciens* strains carrying disarmed Ti plasmids such as strains LBA4404, GV3101, and AGL1 or into *A. rhizogenes* strains such as R4 or NCCP1885. These *Agrobacterium* strains can then be co-cultivated with suitable plant explants or intact plant tissue and the transformed plant cells and/or regenerants selected by using antibiotic resistance (Examples 12 and 13). The expression of the MiAMP1 protein in the transgenic plants can be detected using either antibodies raised to the protein or using anti-microbial bioassays. A second method of gene transfer to plants can be achieved by direct insertion of the gene in target plant cells. For example, the MiAMP1 encoding gene cassette can be co-precipitated onto gold or tungsten particles along with a plasmid encoding a chimeric gene for antibiotic resistance in plants. The tungsten particles can be accelerated using a fast flow of helium gas and the particles allowed to bombard a suitable plant tissue. This can be an embryogenic cell culture, a plant explant, a callus tissue or cell suspension or an intact meristem. Plants can be recovered using the antibiotic resistance gene for selection and antibodies used to detect plant cells expressing the MiAMP1 protein. These and other related methods for the expression of the MiAMP1 in plants are described in "Plant Molecular Biology" (2nd ed., edited by Gelvin, S. B. and Schilperoort, R. A.,© 1994 published by Kluwer Academic Publishers, Dordrecht, The Netherlands).

Both monocotyledonous and dicotyledonous plants can be transformed and regenerated. Plants which can be genetically modified include grains, forage crops, fruits, vegetables, oil seed crops, palms, forestry, and vines. Specific examples of plants which can be modified follow: maize, banana, peanut, field peas, sunflower, tomato, canola, tobacco, wheat, barley, oats, potato, soybeans, cotton, carnations, sorghum, lupin and rice. These, as well as other agricultural plants, can be transformed with the anti-microbial genes such that they exhibit a greater degree of resistance to pathogen attack. Alternatively, the proteins can be used for the control of diseases by topological application.

The invention also relates to application of anti-microbial protein in the control of pathogens of mammals including humans. The protein can be used either in topological or intravenous applications for the control of microbial infections.

*Macadamia integrifolia* Anti-microbial Protein (MiAMP1)

As indicated above, a new class of potent anti-microbial protein (isolated from the seeds of *Mi*) has been identified and characterised. The class includes a particular protein factor, called MiAMP1 as defined above. The protein is highly basic with a predicted pI value of 10.1 and contains 6 cysteine residues (Examples 8 and 9) which are presumed to be important in stabilising the three-dimensional structure of the protein through the formation of disulfide bonds. Additionally, the relative molecular mass of the protein has been determined by mass spectrometry which shows it to be 8134±2 Da. The amino acid sequence shares no significant homology with previously described proteins in sequence databases (Swiss Prot and Non-redundant databases) searched using the blast algorithm (Altschul, S. F. et al. [1990] *J. Mol. Biol.* 215:403) making this a hitherto unknown anti-microbial protein. The protein does not fit into any of the previously described classes of anti-microbial proteins from either plant, animal or microbial sources.

The MiAMP1 protein shows a wide range of anti-fungal activity (Example 4). MiAMP1 shows very significant inhibition of fungal growth at concentrations as low as 1 µg/ml for some of the pathogens/microbes against which the protein was tested with $IC_{50}$ values as low as 2 µg/ml. Thus, it can be used to provide protection against several plant diseases. MiAMP1 can be used as a fungicide or antibiotic by application to plant parts. The protein can also be used to inhibit growth of pathogens by expressing it in whole transgenic plants (Example 13). The protein can be used for the control of human pathogens by topological application or intravenous injection. One characteristic of the protein is that the inhibition of some microbes is suppressed by the presence of $Ca^{2+}$ (1 mM).

With specific reference to the embodiments of the invention defined above, a preferred anti-microbial protein in accordance with the first embodiment is MiAMP1. This protein has a sequence corresponding to residues 27 to 102 of the sequence shown in FIG. 6 (SEQ ID NO: 1).

Anti-microbial proteins according to the invention can be isolated by any of the methods known to those of skill in the art including the method exemplified herein. Anti-microbial proteins can be synthesised either chemically or enzymatically. These methods will again be known to those of skill in the art and are described, for example, in Hancock, D. C. et al. (1995) *Mol. Biotech.* 4(1):73–86, and Wong, C. H. and Wang, K. T. (1991) *Experientia* (Basel) 47(11–12): 1123–1129.

A homologue of the FIG. 6 protein is defined as a protein having substantially the same amino acid sequence as the sequence shown in the figure. This means that the majority of residues present in MiAMP1 will be present in a homologue in the same relative position to each other or will be represented by another amino acid residue containing a side chain with similar properties. For example, it is frequently possible to interchange asparagine and aspartic acid; alanine and glycine; serine, threonine and alanine; isoleucine, valine and leucine; as well as lysine and arginine; whereas, cysteine and histidine residues can rarely be substituted with other amino acids (Bordo, D. and Argos, P. [1991] *J. Mol. Biol.* 217:721–729). It will be appreciated by one skilled in the art that a homologue may have many conservative substitutions aside from the examples already mentioned. It will also be appreciated by one of skill in the art that homologues include engineered variants of the prototype anti-microbial protein. Such variants may be engineered to provide protein with enhanced activity relative to the prototype protein or altered properties to give a protein with greater utility. It will be further appreciated that homologues include proteins with amino acid deletions at the amino-terminus, the carboxy-terminus, internally, or any combination of the foregoing, provided that the deletion variant has substantially the same anti-microbial activity as the prototype protein.

With regard to variants in which particular amino acid residues have been replaced, site-directed mutagenesis can be used to identify functionally important residues and amino acid motifs. At least two methods that allow functional regions of proteins to be identified are known to those of skill in the art. These involve either alanine scanning or targeted replacement of specific residues. The methods will now be briefly described.

Alanine scanning mutagenesis (Cunningham, B. C. and Wells, J. A. [1989] *Science*, 244:1081–1085) involves the progressive replacement of specific amino acid residues with an alanyl residue which is believed to result in limited structural alteration of the protein under examination. However, loss of function due to replacement of a native residue with an alanyl residue generally indicates that a functionally of structurally important residue has been altered. Once such a residue has been identified, other replacements can be tested with the goal of developing variants with desirable properties.

Targeted replacement of specific residues typically relies on knowledge of the tertiary structure of a protein or information gained from sequence alignment of the protein of interest with the sequences of other related proteins. In both cases, residues likely to have a functional role can be identified as targets for replacement.

In the present instance, we have been able to identify candidate residues for targeted replacement from the three-dimensional structure of MiAMP1 determined by NMR spectroscopy. This structure is disclosed in Australian Provisional Patent Application No. PQ1335, the entire content of which is incorporated herein by cross reference. Exemplary replacements will be described in detail below.

Variant proteins according to the invention can be prepared by any of the methods known to those of skill in the art. Typically, however, variants are produced by mutagenesis of DNA encoding a prototype protein such as MiAMP1. Methods of mutagenising DNA are described for example, in *Current Protocols in Molecular Biology*, supra.

With reference to the third embodiment of the invention, the term "construct" includes vectors such as plasmids, cosmids, viruses and the like, as well as naked DNA per se. Control elements which can be included in constructs will be known to those of skill in the art. Examples of such elements are promoters, enhancers, polyadenylation signals and transcription terminators.

Reproductive material of a transgenic plant, as recited in the sixth embodiment, includes seeds, progeny plants and clonal material.

As set out in the seventh and eight embodiments of the invention defined above, anti-microbial proteins according to the first embodiment can be included in compositions for administration to plants and mammalian animals. An anti-microbial protein can be present in a composition as a salt of the protein. Such salts will be known to those of skill in the art as will the nature of carriers, diluents or excipients which can be included in compositions. For example, the carrier present in a pharmaceutical composition can be a physiologically compatible buffer such as Hank's or Ringer's solution, physiological saline, a mixture consisting of saline and glucose, and heparinized sodium citrate-citric acid dextrose solution. The pharmaceutical composition can be orally or parenterally administered in accordance with the object of treatment, and can be prepared as a powder, granules, a solution for injection or oral administration, tablets, suppositories, pessaries, ointment, cream, gel or aerosol. Compositions for agricultural use are typically administered by spraying.

Compositions can include other anti-microbial agents in addition to an anti-microbial protein according to the invention. Such agents will typically be an anti-fungal agent.

Non-limiting examples of the invention follow.

EXAMPLE 1

Extraction of Basic Protein From

*Macadamia integrifolia* Seeds

Twenty five kilograms of *Mi* nuts (purchased from the Macadamia Nut Factory, Queensland, Australia) were ground in a food processor (The Big Oscar, Sunbeam) and the resulting meal was extracted for 2–4 hours at 4° C. with 50 L of an ice-cold extraction buffer containing 10 mM $NaH_2PO_4$, 15 mM $Na_2HPO_4$, 100 mM KCl, 2 mM EDTA, 0.75% polyvinylpolypyrrolidone, and 0.5 mM phenylmethylsulfonyl fluoride (PMSF). The resulting homogenate was run through a kitchen strainer to remove larger particulate material and then further clarified by centrifugation (4,000 rpm for 15 min) in a large capacity centrifuge. Solid ammonium sulphate was added to the supernatant to obtain 30% relative saturation and the precipitate allowed to form overnight with stirring at 4° C. Following centrifugation at 4,000 rpm for 30 min, the supernatant was taken and ammonium sulphate added to achieve 70% relative saturation. The solution was allowed to precipitate overnight and then centrifuged at 4,000 rpm for 30 min in order to collect the precipitated protein fraction. The precipitated protein was resuspended in a minimal volume of extraction buffer and centrifuged once again (13,000 rpm×30 min) to remove the undissolved portion. After dialysis (10 mM ethanolamine pH 9.0, 2 mM EDTA and 1 mM PMSF) to remove residual ammonium sulphate, the protein solution was passed through a Q-Sepharose Fast Flow column (5×12 cm) previously equilibrated with 10 mM ethanolamine (pH 9), 2 mM in EDTA.

The collected flowthrough from this column represents the basic (pI>9) protein fraction of the seeds. This fraction was further purified as described in Example 3.

EXAMPLE 2

Anti-microbial Activity Assays

In general, bioassays to assess antifungal and antibacterial activity were carried out in 96-well microtitre plates. Typically, the test organism was suspended in a synthetic growth medium consisting of $K_2HPO_4$ (2.5 mM), $MgSO_4$ (50 µM), $CaCl_2$ (50 µM), $FeSO_4$ (5 µM), $CoCl_2$ (0.1 µM), $CuSO_4$ (0.1 µM), $Na_2MoO_4$ (2 µM), $H_3BO_3$ (0.5 µM), KI (0.1 µM), $ZnSO_4$ (0.5 µM), $MnSO_4$ (0.1 µM), glucose (10 g/l), asparagine (1 g/l), methionine (20 mg/l), myo-inositol (2 mg/l), biotin (0.2 mg/l), thiamine-HCl (1 mg/l) and pyridoxine-HCL (0.2 mg/l). The test organism consisted of bacterial cells, fungal spores (50,000 spores/ml) or fungal mycelial fragments (produced by blending a hyphal mass from a culture of the fungus to be tested and then filtering through a fine mesh to remove larger hyphal masses). Fifty microliters of the test organism suspended in medium was placed into each well of the microtitre plate. A further 50 μl of the test anti-microbial solution was added to appropriate wells. To deal with well-to-well variability in the bioassay, 4 replicates of each test solution were done. Sixteen wells from each 96-well plate were used as controls for comparison with the test solutions.

Unless otherwise stated, the test organism used was *Phytophthora cryptogea* and incubation was at 25° C. for 48 hours. All fungi including yeast were grown at 25° C. and *E. coli* was grown at 37° C. Percent growth inhibition was measured by following the absorbance at 600 nm of growing cultures over various time intervals and is defined as 100 times the ratio of the average change in absorbance in the control wells minus the change in absorbance in the test well divided by the average change in absorbance at 600 nm for the control wells. (i.e. [(avg change in control wells–change in test well)/(avg change in control wells)]×100). Typically, measurements were taken at 24 hour intervals and the period from 24–48 hours was used for % Inhibition measurements.

EXAMPLE 3

Purification of Anti-microbial Protein from

*Macadamia integrifolia* Basic Protein Fraction

The starting material for the isolation of the *Mi* anti-microbial protein was the basic fraction extracted from the mature seeds as described above in Example 1. This protein was further purified by cation-exchange chromatography as shown in FIG. 1.

About 4 g of the basic protein fraction dissolved in 20 mM sodium succinate (pH 4) was applied to an S-Sepharose High Performance column (5×60 cm) (Pharmacia) previously equilibrated with the succinate buffer. The column was eluted at 17 ml/min with a linear gradient of 20 liters from 0 to 2 M NaCl in 20 mM sodium succinate (pH 4). The eluate was monitored for protein by on-line measurement of the absorbance at 280 nm (see FIG. 1) and collected in 200 ml fractions. Portions of each fraction were subsequently tested in the antifungal activity assay at a concentration of 100 μg/ml. Results of this bioassay are included in FIG. 1: shaded bars represent percent inhibition with the most active fraction showing 100% inhibition. Fractionation yielded a number of unresolved peaks eluting between 0.05 and 1 M NaCl. A major peak eluting at about 6 hours into the separation (fractions 31 and 32) showed the most significant anti-microbial activity.

Figure 2:
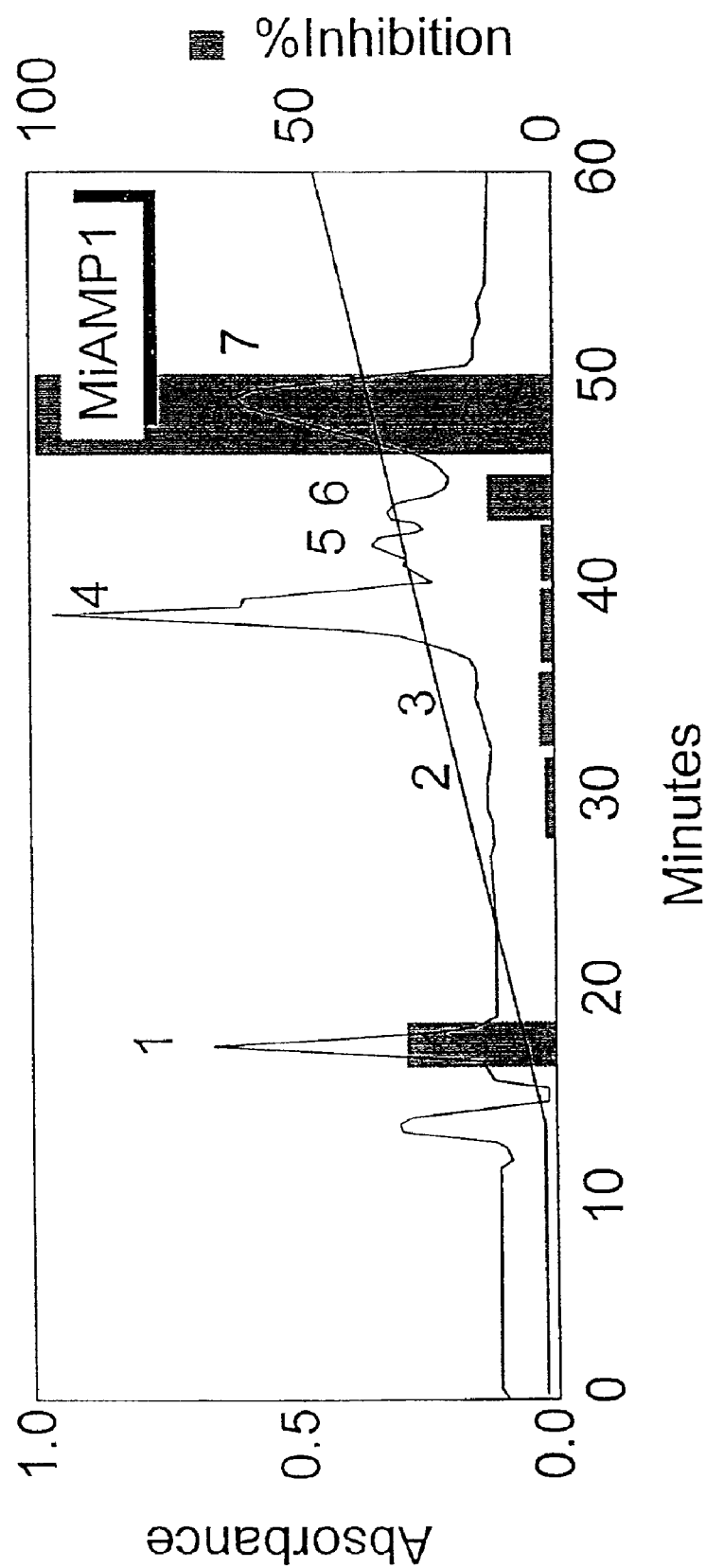
FIG. 2 shows a reversed-phase HPLC profile of the highly inhibitory fractions 31 and 32 taken from the cation-exchange separation and corresponding bioassay data.

The fractions showing significant anti-microbial activity were further purified by reversed-phase chromatography. About 1 mg amounts of combined fractions 31 and 32 were loaded on a Pep-S ($C_2/C_{18}$), column (25×0.93 cm) (Pharmacia) equilibrated with 95% $H_2O$/5% MeCN/0.1% TFA (=100% A). The column was eluted at 3 ml/min with a 300 ml linear gradient (100 min) from 100% A to 5% $H_2O$/95% MeCN/0.1% TFA (=100% B). Individual peaks were manually collected, vacuum dried three times in order to remove traces of TFA, and subsequently resuspended in 500 μl of milli-Q water (millipore corporation water purification system) for use in bioassays as describe in Example 2. FIG. 2 shows the HPLC profile of purified fraction 31/32 from the cation-exchange separation shown in FIG. 1. Protein elution was monitored at 214 nm. Individual peaks were bioassayed for anti-microbial activity: the bars in FIG. 2 show the inhibition corresponding to 100 μg/ml of material from each of the peaks. The active protein constituting peak 7 which elutes at approximately 47 min (35% MeCN) was called MiAMP1.

EXAMPLE 4

Anti-microbial Potency of MiAMP1

MiAMP1 was purified as in Example 3. Anti-microbial potency was tested as described above in Example 2. Table 1 below shows the $IC_{50}$ value of pure MiAMP1 when tested against various fungi and bacteria. In the table, the ">100" indicates that concentrations higher than 100 μg/ml were not tested; "<x" indicates that a concentration less than that value (x) were not tested. The abbreviation "ND" indicates that the test was not performed or that results could not be interpreted. The anti-microbial protein was also tested in the presence of 1 mM $Ca^{2+}$ in the test medium and the $IC_{50}$ values for these tests are given in the left-hand column. As can be seen in the table, the inhibitory activity of MiAMP1 is greatly reduced (although not completely eliminated) in the presence of $Ca^{2+}$.

TABLE 1

Concentrations of MiAMP1 at which 50% inhibition of growth was observed

| Organism | $IC_{50}$ (μg/ml) | $IC_{50}$ + $Ca^{2+}$ |
| --- | --- | --- |
| *Alternaria helianthi* | 2–5 | >100 |
| *Aspergillus fumigatus* | >100 | >100 |
| *Botrytis cinerea* | 2–5 | >100 |
| *Candida albicans* | >100 | >100 |
| *Ceratocystis paradoxa* | 20 | 75 |
| *Colletotrichum falcatum* | >100 | >100 |
| *Colletotrichum gloeosporioides* | 2–5 | >100 |
| *Fusarium oxysporum* | 2–5 | 100 |
| *Leptosphaeria maculans* | 5 | >100 |
| *Macrophomina phaseolina* | <25 | >100 |
| *Microsporum gypseum* | >100 | >100 |
| *Phytophthora cryptogea* | 5–10 | >100 |
| *Pythium graminicola* | 5 | >100 |
| *Sclerotinia sclerotiorum* | 5 | >100 |
| *Sclerotium rolfsii* | >100 | >100 |
| *Verticillium dahliae* | 2–5 | >100 |
| *Saccharomyces cerevisiae* | ND | 1–5 |
| *Clavibacter michiganensis* | <10 | <10 |
| *Pseudomonas rubrilineans* | >100 | >100 |
| *Escherichia coli* | >100 | ND |

EXAMPLE 5

Effect of Purified MiAMP1 on Plant Cells

Since MiAMP1 may be a useful protein to express in transgenic agricultural plants, we tested whether MiAMP1 was toxic to plant cells. Tobacco (*Nicotiana plumbaginofolia*) microcalli culture were cultured in modified CSV media (Gibson, 1976 #219) in the dark with shaking at 110 rpm at 28° C. as per the method described in Gibson et al. (Gibson et al. [1976] *Plant* 128:223–229). Fifty-microliter aliquots of filter-sterilised anti-microbial protein in 1× CSV medium were added to 50 μl plant cell suspensions to obtain a final concentration of 100 μg/ml. After overnight incubation at 28° C., a phenosafranin plus fluorescein diacetate assay was performed to estimate cell viability. Fifty microliter of FDA stock (5 mg/ml in acetone) was added to 2.5 ml of PS stock (0.05% in growth medium) to make the mixed stain (Widholm, J. M. [1972] *Stain Technology* 47:189–194). One drop of the mixed stain was added to one drop of cell suspension and then visualised by brightfield microscopy and by UV excitation microscopy to determine cell viability. A 0.1% solution of Triton X-100 was used as a positive control in these experiments. Tobacco microcalli cultures showed no decline in viability as measured by the number of fluorescing cells (fluorescein diacetate staining) and no increase in the number of dead cells (phenosafranin staining) from exposure to MiAMP1 at concentrations up to 100 μg/ml for up to 72 hours.

EXAMPLE 6

Effect of MiAMP1 on Human Cultured Cells and Red Blood Cells

Toxicity assays were carried out with HeLa cell cultures to investigate the toxicity of MiAMP1 towards human cells. A HeLa cell culture was maintained in a monolayer culture at 37° C. with 5% $CO_2$ in modified RPMI 1640 medium (Trace Biosciences, NSW, Australia). RPMI medium was supplemented with 10% Foetal Bovine Serum (FBS), 2 mM L-glutamine, 2 g/l $NaHCO_3$ plus penicillin G (10,000 U/l) and streptomycin sulphate (100 g/l). One hundred microliter amounts of freshly harvested and diluted cells were transferred to microtitre plates ($10^4$–$10^5$ cells per well). After cells had become attached and almost confluent, the supernatant was removed and replaced with 100 μl filter sterilised anti-microbial protein previously suspended in 1× cell-culture media. Up to 1 mg/ml concentrations of anti-microbial protein were added in triplicate to wells containing a monolayer of HeLa cells and the cultures were then incubated overnight at 37° C. with 5% $CO_2$. Cells were also incubated in the presence of hordothionin at concentrations of 10–400 μg/ml as positive controls. After incubation, the supernatant was removed, the cells rinsed with 2× phosphate buffered saline (1.5 mM $KH_2PO_4$, 8 mM $K_2HPO_4$, 2.7 mM KCl, 135 mM NaCl at 37° C.), and then stained with neutral red dye (Terras, F. R. G. et al. [1992] *J. Biol. Chem.* 267:15301–15309). The culture supernatant was also tested for lactate dehydrogenase (LDH) activity as a measure of cell death (Legrand [1992] *J. Biotech.* 25:231–243). In addition to testing in normal media, cells were also tested in media lacking FBS because of the possibility that FBS might mask toxicity.

Cell viability or proliferation was not affected at concentrations as high as 1 mg/ml as evidenced by microscopic examination and quantitation of dye uptake after staining. In contrast, hordothionin (a protein known to be antibiotic towards human cells) caused a complete loss of cell viability at concentrations of 10 μg/ml and higher. The lack of effect on cell viability by MiAMP1 was confirmed by measuring LDH levels in culture supernatants which showed no change in levels.

In addition to cell viability assays, haemolytic assays were performed with human erythrocytes according to Cammue (Cammue, B. P. A. et al. [1995] *Plant Physiol.* 109:445–455). Human erythrocytes were washed several times by resuspending the cells in 10 mM phosphate, 120 mM NaCl, 27 mM KCl (pH 7.2), gently mixing and settling the cells with mild centrifugation (3 min, 300 g). When supernatant exhibited no visible discolouration, the cells were resuspended in PBS to obtain a 0.5% suspension. Aliquots of 100 μl were added to microtitre plate wells. Protein solutions (100 μl) were added to individual wells to achieve final concentrations of 10–500 μg/ml. Triton X-100 (0.05% final concentration) was used as a positive control for haemolysis and water was used as a negative control. Cell suspensions were incubated for 1 hr at 37° C., the microtitre plate was centrifuged at 300 g, 10° C., for 5 min and supernatant was transferred to a fresh plate whereupon the absorbance (405 nm) was measured. These tests showed no lysis of red blood cells upon exposure to MiAMP1 at concentrations up to 100 μg/ml. The results contrast with thionin anti-microbial peptides (e.g. hordothionin) which have been reported to cause disruption of cultured erythrocytes at concentrations of 5–40 μg/ml (Terras, F. R. G. et al. [1992] *J. Biol. Chem.* 267:15301–15309).

EXAMPLE 7

Purity of Isolated MiAMP1

Figure 3:
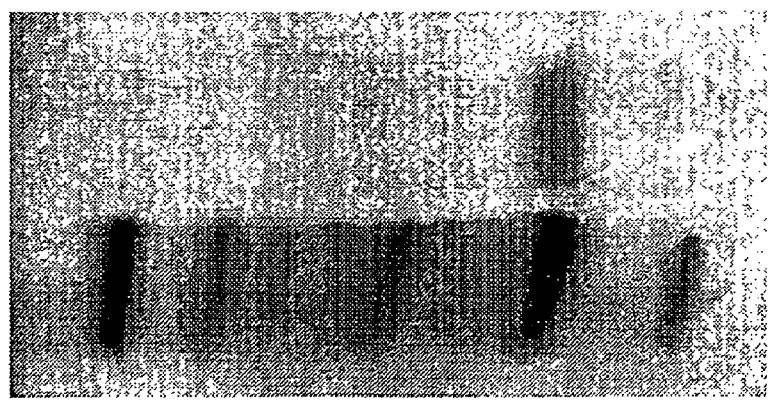
FIG. 3 shows an SDS-PAGE analysis of purified MiAMP1.

The purity of the isolated anti-microbial protein was verified by native SDS-PAGE followed by staining with coomassie blue protein staining solution (see FIG. 3). Electrophoresis was performed on a 10–20% tricine gradient gel (Novex) as per the manufacturers recommendations (100 V, 1–2 hour separation time). Standards (Kaleidascope polypeptide standards, Biorad) were included in lane 3 in order to determine an approximate molecular weight of the protein.

It can be seen from FIG. 3 that the purified MiAMP1 migrates at approximately 8 kDa next to the aprotinin in the molecular weight standards (M.W. of standards occurring from top to bottom in FIG. 3: 38.6 kDa, 25.0 kDa, 16.3 kDa, 7.8 kDa, 3.4 kDa). The detection of a single major band in the SDS-PAGE analysis together with single peaks eluting in analytical cation-exchange and reversed-phase separations (not shown), gives strong indication that the activity of the MiAMP1 was due to the purified protein alone and not to a minor contaminating component.

EXAMPLE 8

Mass Spectroscopic Analysis of MiAMP1

Figure 4:
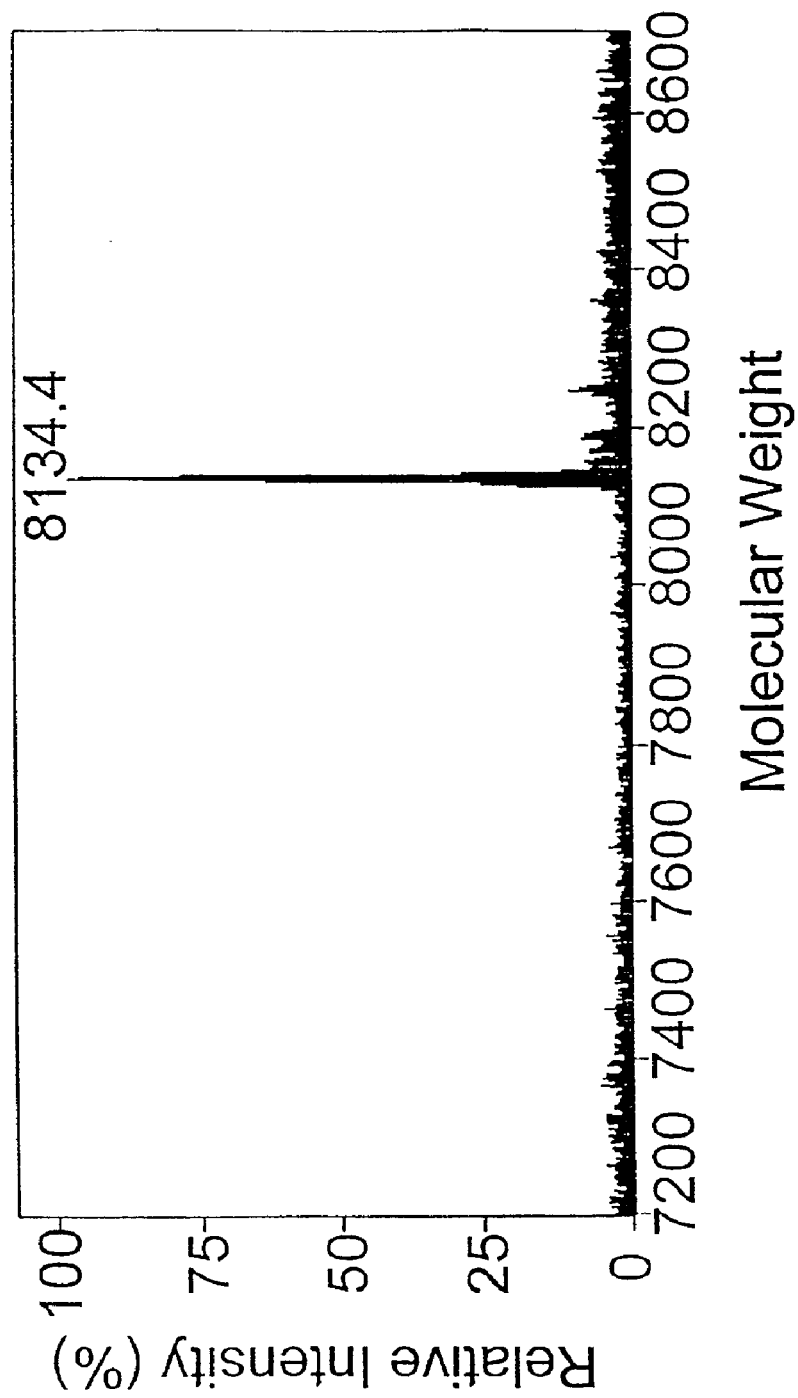
FIG. 4 shows the results of a mass spectrometric analysis of MiAMP1.
Figure 5:
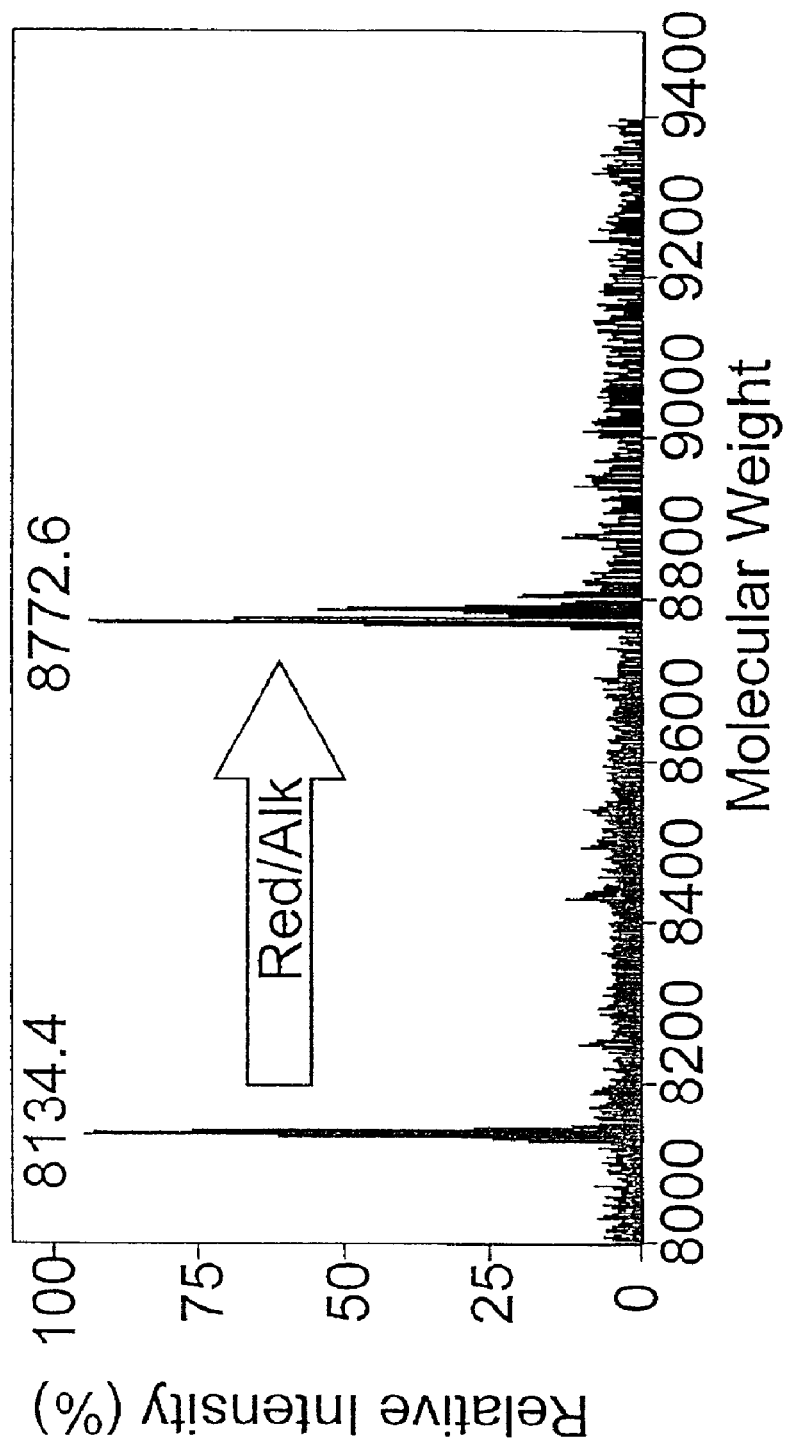
FIG. 5 depicts the results of a mass spectrometric analysis of reduced and alkylated MiAMP1.

Purified MiAMP1 was submitted for mass spectroscopic analysis. Approximately 1 μg of protein in solution was used for testing. Analysis showed the protein to have a molecular weight of 8134 Da±2 Da (see FIG. 4). Additionally, the protein was subjected to reduction of disulfide bonds with dithiothreitol and alkylation with 4-vinylpyridine. The product of this reduction/alkylation was then also submitted for mass spectroscopic analysis and was shown to have gained 638 mass units (i.e. molecular weight was increased to 8773±2 Da—see FIG. 5). The gain in mass was interpreted as indicating that six 4-vinylpyridine groups (mass 106 Da) had reacted with the reduced protein, indicating that the protein contains a total of 6 cysteine residues. The cysteine content has also been subsequently confirmed through amino acid and nucleotide sequencing (see Example 9 and 11).

EXAMPLE 9

Amino Acid Sequence of MiAMP1

Approximately 1 µg of the pure protein which had been reduced and alkylated was subjected to Automated Edman degradation N-terminal sequencing. In a first sequencing run, 35 residues of the sequence were determined. Subsequently, MiAMP1 was digested with the endoproteinase Lys-C which cleaves after the carboxyl group of lysyl residues. One milligram of reduced/alkylated protein was digested with Lys-C (Boehringer Mannheim) as per manufacturers instructions. Fragments were purified by reversed-phase HPLC and sequenced. Using this digest, the sequence of the protein was determined up to residue 68. Further digestion of the Lys-C fragment with the endoproteinase trypsin (TPCK treated, Sigma) yielded two fragments. Subsequent sequencing provided an additional 2 residues of sequence to give 70 residues of the partial sequence (see FIG. 6 for full sequence of the mature protein). Subsequently, the remaining 6 amino acids were deduced from the DNA sequence (see Example 8) to yield the entire protein sequence of 76 amino acid residues. FIG. 6 shows the sequence of the mature protein (boxed) as well as the sequence of the signal peptide (underlined) determined from the cDNA sequence (Example 8). The ATG start of translation and TAG stop codons are also underlined in the nucleotide sequence shown above the amino acid sequence. The amino acid sequence of the protein having been determined, it was possible to predict the mass of the protein. Using the software program MacVector 4.5.3, a predicted mass of 8137.51 Da was obtained. Depending on the number of disulfide bonds that are formed, the protein mass will range from 8131.5 to 8137.5 Da. This is in close agreement with the mass of 8134.4±2 Da obtained by mass spectrometric analysis (Example 5) even if the protein presumably forms 3 disulfide bonds (lowering the mass by 6 Da). Since the mass of the protein measured by mass spectrometry and the mass calculated from the amino acid sequence agreed almost exactly, the amino acid sequence was judged to be accurate.

EXAMPLE 10

Identification of Related Proteins in Other Excisions of the Family Proteaceae Rabbits were immunised intramuscularly according to standard protocols with MiAMP1 conjugated to diphtheria toxoid suspended in Fruends incomplete adjuvent. Serum was harvested from the animals at regular intervals after giving the animal added doses of MiAMP1 adjuvent to boost the immune response. Approximately 100 ml of serum were collected and used for screening of crude extracts obtained from several plant seeds. One hundred gram quantities of seeds were ground and extracted to obtain a crude extract as in Example 1. Aliquots containing 5 and 50 µg amounts of protein were separated on SDS-PAGE gels and the gels were then blotted onto nitrocellulose membrane for subsequent detection of antigenic proteins. The membranes were incubated with MiAMP1 rabbit primary antibodies, washed and then incubated with alkaline phosphatase-conjugated goat anti-rabbit IgG for colorimetric detection of antigenic bands using the chemical 5-bromo-4-chloro-3-indolyl phosphate/ nitroblue tetrazolium substrate system (Schleicher and Schuell). A stained membrane is depicted in FIG. 7.

Figure 7:
FIG. 7 depicts a western blot of protein extracts from various Proteaceae species using rabbit antiserum to MiAMP1.

FIG. 7 shows that various Proteaceae species contain antigenically-related proteins of similar size to MiAMP1. Lanes 1–22 contain the following extracts: 1) *Persoonia levis,* 2) *Stirlingia simplex,* 3) *Isopogon trilobus,* 4) *Protea pulchra,* 5) *Cardwellia sublimis,* 6) *Stenocarpus sinuatus,* 7) *Telopea oreades,* 8) *Xylomelum protocea,* 9) *Macadamia integrifolia,* 10) *Grevillea robusta,* 11) *Hakea platysperma,* 12) *Banksia asplenifolia,* 13) *Banksia robur,* 14) MiAMP1 (pure), 15) rice, 16) barley, 17) chickpea, 18) mungbean, 19) *Flindersia australis,* 20) radish, 21) canola, 22) MiAMP1 (pure). Lanes 1–14 contain extracts from the family Proteaceae and all show the presence of antigenically related proteins of a similar size to MiAMP1 (including a very weak signal in lane 2 which did not photograph well). The control lanes (15–21) containing extracts from unrelated species do not show any proteins of similar size and antigenicity.

Bioassays were also performed using several crude extracts from Proteaceae species. Specifically, extracts from *Banksia robur, Banksia canei, Hakea gibbosa, Stenocarpus sinuatus, Stirlingia latifolia* and *Macadamia integrifolia* have all been shown to exhibit anti-microbial activity.

EXAMPLE 11

Molecular Cloning of DNA Encoding MiAMP1

Degenerate primers corresponding to the reverse-translated nucleotide sequence were used in reverse-transcriptase PCR reactions (primer α sequence 5' CCG AAG CAG TTG CA[C/G/T] GC[C/G/T] C 3' [SEQ ID NO: 3] and primer β sequence 5' GAG [C/A]G[T/G] TAT [T/A] [C/G][T/G] AAG TGT GG 3' [SEQ ID NO: 4]). PCR products were then directly sequenced (ABI PRISM Dye Terminator Cycle Sequencing Ready Reaction Kit from Perkin Elmer Corporation) after excising DNA bands from agarose gels and purifying them using a Qiagen DNA clean-up kit. Using this approach, we were able to amplify a 160 base-pair fragment of DNA from mRNA of *Mi* kernels using cDNA as a template in the polymerase chain reaction. Specific oligonucleotide primers were then designed from this nucleotide sequence for use in 5' and 3' rapid amplification of cDNA ends (RACE). The 3' RACE protocol utilised a specific primer derived from the known nucleotide sequence (primer α, 5' TGC TCT CTA CAA CCA GGC TG 3'; SEQ ID NO: 5 ) together with an oligo d(T)$_{25}$ primer (primer β) to amplify a fragment corresponding to the 3' end of the cDNA (FIG. 6, positions 334–493). The 5' RACE protocol made use of another specific primer (primer β, 5' GCA TTG GAT GAA GAT ACT C-3'; SEQ ID NO: 6) derived from the known sequence in combination with a primer (primer α, 5'-GGC CAC GCG TCG ACT AGT ACG GGI IGG GII GGG IIG-3'; SEQ ID NO: 7) designed to efficiently anneal to poly-C-tailed cDNA used in the 5'

RACE protocol (Frohman, M. A. [1990] "RACE: Rapid amplification of cDNA ends", in *PCR Protocols, a Guide to Methods and Applications*, Innis, M. A., Gelfan, D. H., Sninsky, J. J. and White, T. J. eds, pp. 28–38, Academic Press, London). The 5' RACE protocol led to the determination of bases 1–282 (FIG. 6). Subsequently, two specific primers corresponding to the 5' and 3' ends of the gene were synthesised and used to amplify a near full-length nucleotide fragment (FIG. 6, positions 15–481) which was ligated directly into the cloning site of a pGEM-T vector (Promega) for further manipulations and sequencing.

EXAMPLE 12

Construction of the Plant Transformation Vector pPCV91-MiAMP1

Figure 8:
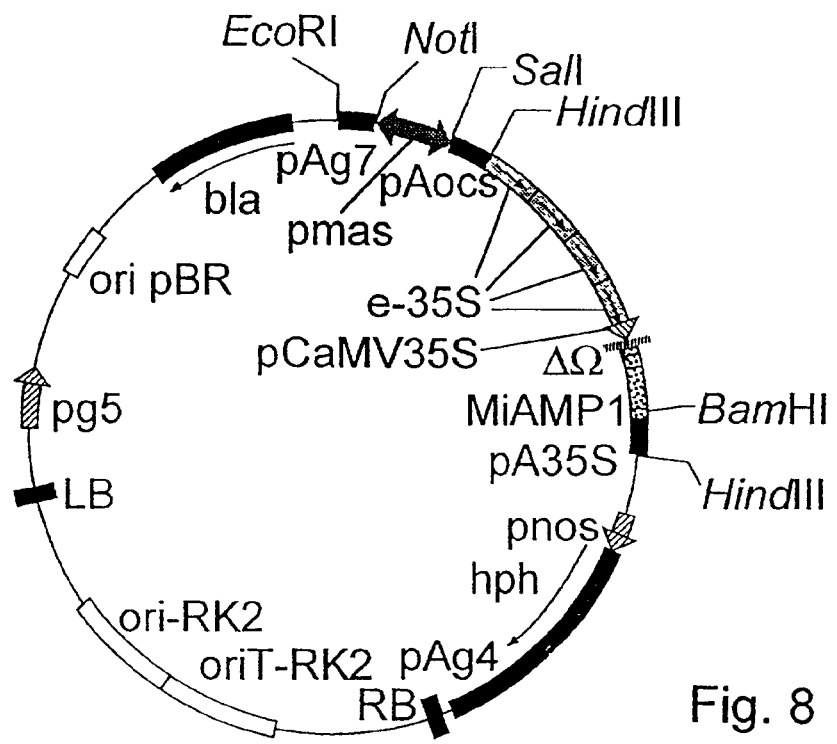
FIG. 8 is a map of the plasmid pPCV91-MiAMP1.

The expression vector pPCV91-MiAMP1 (FIG. 8) contains the full coding region of the MiAMP1 DNA flanked at it 5' end by the strong constitutive promoter of 35S RNA from the cauliflower mosaic virus (pCaMV35S) (Odel et al., [1985] *Nature* 313: 810–812) with a quadruple-repeat enhancer element (e-35S) to allow for high transcriptional activity (Kay et al. [1987] *Science* 236:1299–1302). The coding region of MiAMP1 DNA is flanked at its 3' end by the polyadenylation sequence of 35S RNA of the cauliflower mosaic virus (pA35S). The plasmid backbone of this vector is the plasmid pPCV91 (Walden, R. et al. [1990] *Methods Mol. Cell. Biol.* 1:175–194). The plasmid also contains other elements useful for plant transformation such as an ampicillin resistance gene (bla) and a hygromycin resistance gene (hph) driven by the nos promoter (pnos). These and other features allow for selection in various cloning and transformation procedures. The plasmid pPCV91-MiAMP1 was constructed as follows: The PCR-cloned fragment in the pGEM-T vector (Example 11) was digested using restriction enzymes Sac II and Spe I to release the MiAMP1 gene fragment. The binary vector pPCV91 was digested with the restriction enzyme Bam HI. Both the MiAMP1 DNA fragment and the binary vector were then treated with T4 DNA polymerase to blunt the overhangs. Subsequently, the two fragments were ligated using T4 DNA ligase to produce pPCV91-MiAMP1 binary vector for plant transformation (FIG. 8).

EXAMPLE 13

Plant Transformation

The disarmed *Agrobacterium tumefaciens* strain GV3101 (pMP90RK) (Koncz, C. S.[1986] *Mol. Gen. Genet.* 204:383–396) was transformed with the vector pPCV91-MiAMP1 (Example 12) using the method of Walkerpeach et al. (Walkerpeach, C. R. et al. [1994] *Plant Mol. Biol. Manual* B1:1–19) adapted from Van Haute (Van Haute, E. et al. [1983] *EMBO J.* 2:411–417).

Tobacco transformation was carried out using leaf discs of *Nicotiana tabacum* based on the method of Horsch et al. (Horsch et al. [1985] *Science* 227:1229–1231) and co-culturing strains containing pPCV91-MiAMP1. After co-cultivation of Agrobacterium and tobacco leaf disks, transgenic plants (transformed with pPCV91-MiAMP1) were regenerated on media containing 50 µg/ml hygromycin and 500 µg/ml Cefotaxime. These transgenic plants can be analysed for expression of the newly introduced genes using standard western blotting techniques. Plants capable of constitutive expression of the introduced genes can be selected and self-pollinated to give seed. F1 seedlings of the transgenic plants can be further analysed.

EXAMPLE 14

Construction of the Bacterial Expression Vector pET-MiAMP1

Figure 9:
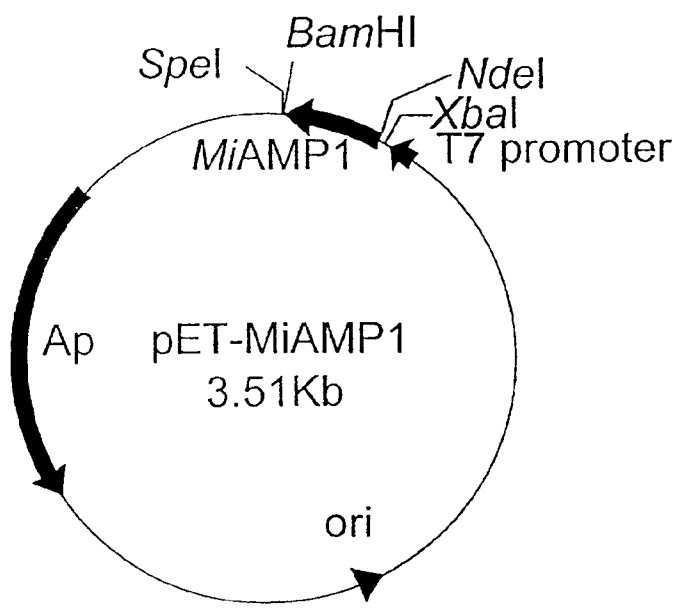
FIG. 9 is a map of the plasmid pET-MiAMP1.
Figure 12:
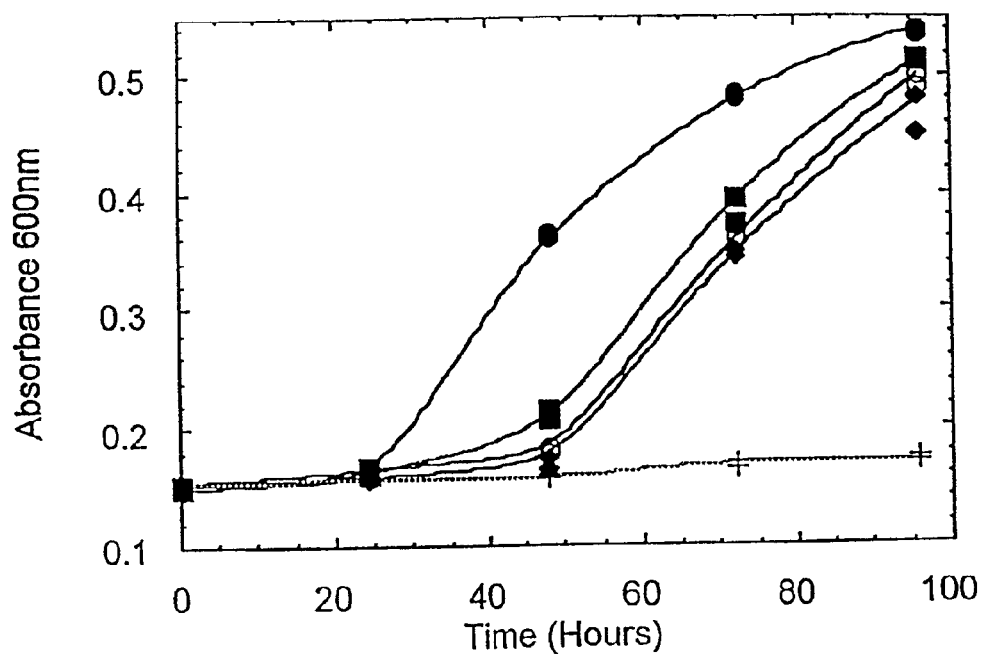
FIG. 12. is a graph showing the effect of variants of MiAMP1 on the growth of *Verticillium dahliae*. Growth curves included in the figure are as follows: control *V. dahliae*, ( ); native MiAMP1, ( ); Mi54K variant, (▲); Mi46K variant, ( ); and Mi46K/54V variant, (+). All proteins were added at a concentration of 5 µg/ml and growth was monitored at 24 hour intervals over 96 hours.

PCR primers flanking the coding region of the MiAMP1 gene were engineered to contain restriction sites for Nde I and Bam HI (corresponding to the 5' and 3' ends of the coding region, respectively). These primers were then used to amplify the coding region of MiAMP1 cDNA. After digestion with Nde I and Bam HI, the PCR product from this amplification was then ligated into a pET-17b vector (Novagen/Studier, F. W. et al. [1986] *J. Mol. Biol.* 189:113) with the coding region in-frame to produce the vector pET-MiAMP1 (FIG. 9).

EXAMPLE 15

Expression of MiAMP1 Protein in Liquid Culture

*E. coli* strain BL21 (Grodberg, J. [1988] *J. Bacteriol.* 170:1245) transformed with the vector pET-MiAMP1 (Example 14) was cultured to an optical density of 0.6 and induced with the addition of 0.4 mM IPTG (isopropyl-β-D-thiogalactopyranosid). Aliquots of the growing culture were removed at timed intervals and protein extracts run on an SDS-PAGE gel to follow the expression levels of MiAMP1 in the culture.

Figure 10:
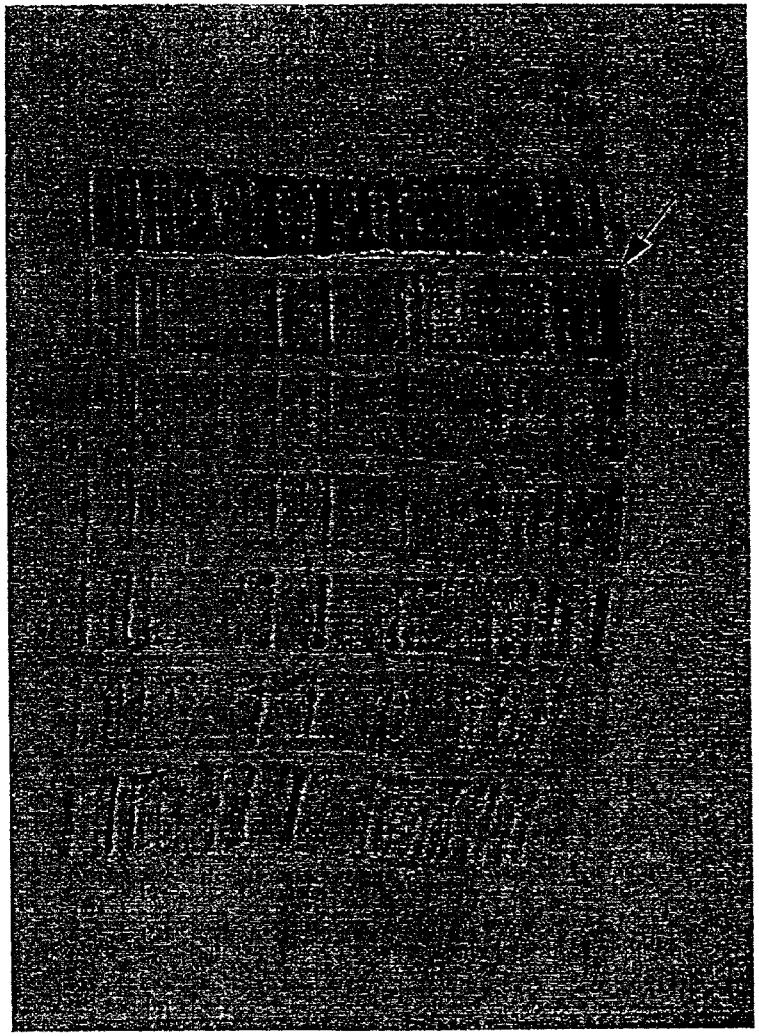
FIG. 10 depicts a stained SDS-PAGE gel used to analyse samples from cultures of transformed and non-transformed *E. coli*.

FIG. 10 shows the SDS-PAGE analysis of the extracts obtained following induction. Lane 1 contains molecular weight markers. Lanes 2–7 contain extracts from the culture at 0, 1, 2, 3, 4, and 5 hours after induction. Lane 8 contains extract from a non-transformed *E. coli* strain BL21. Lane 9 contains pure MiAMP1. The arrow in FIG. 10 highlights the band of MiAMP1 protein produced in the culture. A dramatic accumulation in the levels of MiAMP1 following induction is evident.

EXAMPLE 16

MiAMP1 Variants

In this example, we describe the production of MiAMP1 variants with enchanced anti-microbial activity.
Mutagenesis Procedure The MiAMP1 coding sequence (see SEQ ID NO: 2) was mutagenised by three sequential PCRs as schematically shown in FIG. 11. To provide the desired variants, mismatched primers as set out in Table 2 were employed. In the table, the residue numbering relates to the mature MiAMP1 protein. The first residue is thus the Ser at position 27 of SEQ ID NO: 1. The single letter amino acid code is used to define mutations with the letter before the position number being the native residue and the letter after the number being the new residue. In the mismatched oligonucleotide primer sequences, the nucleotides corresponding to the mutated codon are presented in bold type.

TABLE 2

Sequences of Mismatched Oligonucleotide Primers
Used to Generate Mutagenised Coding Regions

| Primer Name | Mutation | Oligonucleotide Sequence | SEQ ID NO: |
|---|---|---|---|
| Mi28K | Q28K | 5' GCT ATA CAT AAA AAG GGA GG 3' | 8 |
| Mi39K | Q39K | 5' TAC ACT GGA AAA ACT GCT GC 3' | 9 |
| Mi46K | Q46K | 5' GCA TCC AGC TTT GTT GTA GAG AGC 3' | 10 |
| Mi54V | H54V | 5' GGT GTT GCA GTG ACC AGG TTT GGG 3' | 11 |
| Mi54K | H54K | 5' GGT GTT GCA AAA ACC AGG TTT GGG 3' | 12 |

The procedure also used a 5' or 3' primer from the coding region of MiAMP1. The 5' primer, which was designated "Mi1", had the following sequence:

5'-ACA CCA TAT GAG TGC ATT TAC AGT ATG AGT G-3' (SEQ ID NO: 13)

The sequence of the 3' primer, "Mi2", was as follows:

5'-GAA GAG TAT CTT CAT CCA ATG CTA AGG ATC CAC AC-3' (SEQ ID NO: 14)

The first round PCR (30 cycles, 15 sec at 95° C., 15 sec at 50° C., 1 min at 72° C.) involved amplification of a fragment using a mismatched primer (Table 2) together with either Mi1 or Mi2, depending on the orientation of the mismatched primer. The amplification product containing the mismatched codon was used to prime a second round assymetric PCR amplification (as above) together with a complementary Mi1 or Mi2 primer. A final amplification was performed using Mi1 and Mi2 to amplify the mutated insert to allow cloning. The amplification products were then digested with NdeI/BamHI and ligated into pSBETa digested with the same enzymes. The plasmid pSBETa is a composite vector composed of the T7 promoter and cloning site from pET6A (Novagen Inc) cloned into the pSB161 vector described by P. Schenk et al. (1995) *Biotechniques*, 19:196–200. The ligated vectors were then transformed into *E. coli* essentially as described above in Example 15. The insert sequence in the ligated vector was verified by nucleotide sequence analysis.

The above mutagenesis procedure using the mismatched primers defined in Table 2 provided five variant proteins with single amino acid residue substitutions. In addition, two combination variants based on the Q46K mutation were produced. In one of the combination variants, a lysyl residue was substituted for the histidyl residue at position 54—a H54V mutation. The variants were named according to the substitution. Thus, Mi28K is the variant having a lysyl substitution at position 28 of mature MiAMP1. The combination variant Mi46K/54V is the variant having a lysyl substitution at position 46 and a valyl substitution at position 54. Sequence identifications of the variant proteins follow:

| | |
|---|---|
| Mi28K | SEQ ID NO: 15 |
| Mi39K | SEQ ID NO: 16 |
| Mi46K | SEQ ID NO: 17 |

-continued

| | |
|---|---|
| Mi54V | SEQ ID NO: 18 |
| Mi54K | SEQ ID NO: 19 |
| Mi46K/54V | SEQ ID NO: 20 |
| Mi46K/54K | SEQ ID NO: 21 |

Production of Variants

*E. coli* (BL21) transformed with pSBETa was grown and induced, and the insoluble protein fraction obtained after cell lysis as described in Example 15. The insoluble protein extract obtained as described above was dialysed, adjusted to pH 6 by addition of $^1/_{25}$ volume of 500 mM 2-[morpholino]ethanesulphonic acid (MES) pH 6, and applied to a Resource S (1 mL) column (Pharmacia) previously equilibrated with 20 mM MES pH 6. Gradients were run (30 min at 1 mL per minute) from 0–2 M NaCl, and the eluate was monitored for protein by absobance at 280 nm and collected in 1 mL fractions. The remainder of the protein purification was performed as described in Harrison, S. J. et al. (1999) *Protein Expression and Purification*, 15:171–177. The purity of the variant proteins was assessed by analytical HPLC and the amino acid substitution or substitutions confirmed by mass spectrometry.

Anti-microbial Activity and Other Properties of Variants

The antimicrobial activity of variants of MiAMP1 were assessed against *Verticillium dahliae*, *Sclerotinia sclerotiorum*, *Fusarium oxysporum*, *Alternaria brassicicola* and *Saccharomyces cerevisiae*. The $IC_{50}$ value for each variant was calculated over a standard 24–48 hour period of growth as well as over a 0–96 hour period to determine if the variants had developed improved antimicrobial activity across a fuller growth period compared to the native peptide. Because we found that anti-microbial activity of native MiAMP1 was significantly reduced against both *Verticillium dahliae* and *Sclerotinia sclerotiorum* in the presence of 1 mM $Ca^{2+}$, variants were also assayed against these two fungi in the presence of elevated concentrations of $Ca^{2+}$. To examine the effect of $Ca^{2+}$ critically, bioassays were performed against these two fungi in the presence of both 0.1 mM and 1 mM $Ca^{2+}$. Assays of anti-microbial activity were carried out essentially as described in Example 2.

Anti-microbial activities determined for the single substitution variants are presented in Tables 3 and 4. In each table, a comparison is made with MiAMP1 isolated from nut kernals-MiAMP1 (N)—or expressed in *E. coli* and purified therefrom—MiAMP1 (R).

TABLE 3

IC$_{50}$ values for MiAMP1 variants over a 24–48 hour assay period

| Protein tested | V. Dahliae | S. sclerotiorum | F. oxysporum | A. brassicicola | S. cerevisiae |
|---|---|---|---|---|---|
| MiAMP1 (N) | 10 | 10 | 10 | 50 | 5 |
| MiAMP1 (R) | 10 | 10 | 10 | 50 | 5 |
| Mi28K | 4 | 7.5 | 8 | 60 | 4 |
| Mi39K | 5 | 10 | 10 | 50 | 5 |
| Mi46K | 6 | 6 | 5 | 50 | 4 |
| Mi54V | 1.5 | 3 | 7 | 7.5 | 2 |
| Mi54K | 3 | 4 | 5 | 10 | 3 |

TABLE 4

IC$_{50}$ values for MiAMP1 variants over a 96 hour assay period

| Protein tested | V. Dahliae | S. sclerotiorum | F. oxysporum | A. brassicicola | S. cerevisiae |
|---|---|---|---|---|---|
| MiAMP1 (N) | 50 | >100 | >100 | >100 | 10 |
| MiAMP1 (R) | 50 | >100 | >100 | >100 | 10 |
| Mi28K | 25 | 50 | >100 | >100 | 20 |
| Mi39K | 50 | >100 | >100 | >100 | 40 |
| Mi46K | 15 | 25 | >100 | >100 | 10 |
| Mi54V | 50 | 5 | >100 | 80 | >100 |
| Mi54K | 12 | 10 | >100 | 50 | 10 |

The results obtained with the combination variants are presented in Table 5.

TABLE 5

IC$_{50}$ values for MiAMP1 variants over 24–48 and 96 hour assay periods

| | Verticillium dahliae | | Fusarium oxysporum | |
|---|---|---|---|---|
| Protein tested | 24–48 hours | 0–96 hours | 24–48 hours | 0–96 hours |
| MiAMP1 | 10 | 50 | 10 | >100 |
| Mi46K/54V | <1 | <1 | <1 | 5 |
| Mi46K/54K | <1 | <1 | <1 | 3 |

The results presented in Tables 3 to 5 show that the amino acid substitutions comprising the variants enhanced antimicrobial activity relative to the native protein. The combination variants in particular gave remarkably enhanced activity against *V. dahliae* and *F. oxysporum*.

Data on the susceptibility of the variants to calcium ions are presented in Tables 6 and 7.

TABLE 5

IC$_{50}$ values for MiAMP1 variants over a 24–48 hour assay period when assayed in the presence of calcium ions

| | Verticillium dahliae | | | Sclerotinia sclerotiorum | | |
|---|---|---|---|---|---|---|
| Protein tested | 0.05 mM CaCl$_2$ | 0.1 mM CaCl$_2$ | 1 mM CaCl$_2$ | 0.05 mM CaCl$_2$ | 0.1 mM CaCl$_2$ | 1 mM CaCl$_2$ |
| MiAMP1 (N) | 10 | 30 | 90 | 10 | 50 | >100 |
| MiAMP1 (R) | 10 | 30 | 90 | 10 | 50 | >100 |
| 28K | 4 | 10 | 15 | 7.5 | 35 | 80 |
| 39K | 5 | 30 | 85 | 10 | 50 | >100 |
| 46K | 6 | 8 | 10 | 6 | 15 | 75 |

TABLE 5-continued

IC$_{50}$ values for MiAMP1 variants over a 24–48 hour assay period when assayed in the presence of calcium ions

| | IC$_{50}$ (µg/ml) | | | | | |
|---|---|---|---|---|---|---|
| | Verticillium dahliae | | | Sclerotinia sclerotiorum | | |
| Protein tested | 0.05 mM CaCl$_2$ | 0.1 mM CaCl$_2$ | 1 mM CaCl$_2$ | 0.05 mM CaCl$_2$ | 0.1 mM CaCl$_2$ | 1 mM CaCl$_2$ |
| 54V | 1.5 | 25 | 60 | 3 | 10 | 50 |
| 54K | 3 | 3 | 5 | 4 | 10 | 35 |

TABLE 7

IC$_{50}$ values for MiAMP1 variants over a 96 hour assay period when assayed in the presence of calcium ions

| | IC$_{50}$ (µg/ml) | | | | | |
|---|---|---|---|---|---|---|
| | Verticillium dahliae. | | | Sclerotinia sclerotiorum | | |
| Protein tested | 0.05 mM CaCl$_2$ | 0.1 mM CaCl$_2$ | 1 mM CaCl$_2$ | 0.05 mM CaCl$_2$ | 0.1 mM CaCl$_2$ | 1 mM CaCl$_2$ |
| MiAMP1 (N) | 50 | >100 | >100 | >100 | >100 | >100 |
| MiAMP1 (R) | 50 | >100 | >100 | >100 | >100 | >100 |
| 28K | 25 | 25 | >100 | 50 | 45 | >100 |
| 39K | 50 | 80 | >100 | >100 | >100 | >100 |
| 46K | 15 | 20 | >100 | 25 | 30 | >100 |
| 54V | 50 | 60 | >100 | 5 | 15 | >100 |
| 54K | 12 | 15 | >100 | 10 | 15 | >100 |

The results presented in Tables 6 and 7 clearly show that the variants are less susceptible to calcium ion suppression than the native protein.

The effect of variant proteins on the growth of *V. dahliae* is presented graphically in FIG. 12. Growth curves included in the figure are as follows: control *V. dahliae*, (●); native MiAMP1, (■); Mi54K variant, (▲); Mi46K variant, (○); and Mi46K/54V variant, (+). All proteins were added at a concentration of 5 μg/ml and growth was monitored at 24 hour intervals over 96 hours.

FIG. 12 shows that the combination variant gives a dramatic increase in anti-microbial potency as compared to the single-residue variants that are nevertheless more potent than native MiAMP1.

It will be appreciated by those of skill in the art that many changes can be made to the embodiments exemplified above without departing from the broad ambit and scope of the invention.

What is claimed is:

1. An isolated or synthetic polynucleotide which encodes an anti-microbial protein selected from the group consisting of:
   (i) a protein comprising residues 27 to 102 of SEQ ID NO: 1, and
   (ii) a variant of (i) having one of the following substitutions: K is substituted for Q at position 54, 65 or 72, V or K is substituted for H at position 80, or K is substituted for Q at position 72 and V or K is substituted for H at position 80.

2. The polynucleotide according to claim 1 comprising nucleotides 148 to 375 of SEQ ID NO: 2.

3. The polynucleotide according to claim 1 which encodes a variant having an amino acid sequence of SEQ ID NO: 20 or SEQ ID NO: 21.

4. The DNA construct comprising the polynucleotide according to claim 1 operatively linked to elements for the expression of the protein encoded by said polynucleotide.

5. The construct according to claim 4, wherein said polynucleotide-comprises nucleotides 70 to 375 of SEQ ID NO: 2.

6. A host cell comprising the DNA construct according to claim 4.

7. The host cell according to claim 6, wherein the cell is selected from the group consisting of a bacterial cell, a fungal cell, an insect cell, a plant cell, and a mammalian cell.

8. A transgenic plant comprising the DNA construct according to claim 4.

9. The transgenic plant according to claim 8, wherein the plant is a monocot or a dicot.

10. The transgenic plant according to claim 9, wherein the plant is selected from the group consisting of grains, forage crops, fruits, vegetables, oil seed crops, palms, trees, and vines.

11. The transgenic plant according to claim 9, wherein the plant is selected from the group consisting of maize, banana, peanut, field pea, sunflower, tomato, canola, tobacco, wheat, barley, oats, potato, soybeans, cotton, carnation, sorghum, lupin and rice.

12. Reproductive material of the transgenic plant of claim 8, wherein the reproductive material comprises the DNA construct.

13. The reproductive material according to claim 12 which is selected from the group consisting of seeds, progeny plants and clonal material.

* * * * *

```
SEQUENCE LISTING

<160> NUMBER OF SEQ ID NOS: 21

<210> SEQ ID NO 1
<211> LENGTH: 102
<212> TYPE: PRT
<213> ORGANISM: Macadamia integrifolia

<400> SEQUENCE: 1

Met Ala Ser Thr Lys Leu Phe Phe Ser Val Ile Thr Val Met Met Leu
 1               5                  10                  15

Ile Ala Met Ala Ser Glu Met Val Asn Gly Ser Ala Phe Thr Val Trp
            20                  25                  30

Ser Gly Pro Gly Cys Asn Asn Arg Ala Glu Arg Tyr Ser Lys Cys Gly
        35                  40                  45

Cys Ser Ala Ile His Gln Lys Gly Gly Tyr Asp Phe Ser Tyr Thr Gly
    50                  55                  60
```

```
Gln Thr Ala Ala Leu Tyr Asn Gln Ala Gly Cys Ser Gly Val Ala His
 65                  70                  75                  80

Thr Arg Phe Gly Ser Ser Ala Arg Ala Cys Asn Pro Phe Gly Trp Lys
                 85                  90                  95

Ser Ile Phe Ile Gln Cys
            100
```

```
<210> SEQ ID NO 2
<211> LENGTH: 493
<212> TYPE: DNA
<213> ORGANISM: Macadamia integrifolia
<220> FEATURE:
<221> NAME/KEY: CDS
<222> LOCATION: (70)...(375)
<223> OTHER INFORMATION: y=t or c.

<400> SEQUENCE: 2
```

```
attaagtctt tgagtctcat acatactctt ctcctcccca ccattagcac ttatcagcta      60 acctcagcc atg gct tcc acc aag ttg ttc ttc tca gtc att act gtg atg    111
          Met Ala Ser Thr Lys Leu Phe Phe Ser Val Ile Thr Val Met
            1               5                  10 atg ctc ata gca atg gca agt gag atg gtg aat ggg agt gca ttt aca      159
Met Leu Ile Ala Met Ala Ser Glu Met Val Asn Gly Ser Ala Phe Thr
 15                  20                  25                  30 gta tgg agt ggt cca ggt tgt aac aac cgt gct gag cga tat agc aag      207
Val Trp Ser Gly Pro Gly Cys Asn Asn Arg Ala Glu Arg Tyr Ser Lys
                 35                  40                  45 tgt gga tgc tca gct ata cat cag aag gga ggc tat gac ttc agc tac      255
Cys Gly Cys Ser Ala Ile His Gln Lys Gly Gly Tyr Asp Phe Ser Tyr
             50                  55                  60 act gga caa act gct gct ctc tac aac cag gct gga tgc agt ggt gtt      303
Thr Gly Gln Thr Ala Ala Leu Tyr Asn Gln Ala Gly Cys Ser Gly Val
 65                  70                  75 gca cac acc agg ttt ggg tcc agt gcc agg gca tgc aac cct ttt ggt      351
Ala His Thr Arg Phe Gly Ser Ser Ala Arg Ala Cys Asn Pro Phe Gly
 80                  85                  90 tgg aag agt atc ttc atc caa tgc tagatttcat aactcttgga tccatcttct     405
Trp Lys Ser Ile Phe Ile Gln Cys
 95              100 atgttttca agtgtataat tagagagatg catggatata taataaataa gtaaaagcta     465
cggtatcacc atgtgatgat tttyaccc                                        493
```

```
<210> SEQ ID NO 3
<211> LENGTH: 19
<212> TYPE: DNA
<213> ORGANISM: Artificial Sequence
<220> FEATURE:
<223> OTHER INFORMATION: Degenerate primer alpha.

<400> SEQUENCE: 3
ccgaagcagt tgcabgcbc                                                  19
```

```
<210> SEQ ID NO 4
<211> LENGTH: 20
<212> TYPE: DNA
<213> ORGANISM: Artificial Sequence
<220> FEATURE:
<223> OTHER INFORMATION: Degenerate primer beta.

<400> SEQUENCE: 4
gagmgktatw skaagtgtgg                                                 20
```

<210> SEQ ID NO 5
<211> LENGTH: 20
<212> TYPE: DNA
<213> ORGANISM: Artificial Sequence
<220> FEATURE:
<223> OTHER INFORMATION: 3' RACE primer alpha.

<400> SEQUENCE: 5
tgctctctac aaccaggctg                                            20

<210> SEQ ID NO 6
<211> LENGTH: 19
<212> TYPE: DNA
<213> ORGANISM: Artificial Sequence
<220> FEATURE:
<223> OTHER INFORMATION: 5' RACE primer beta.

<400> SEQUENCE: 6
gcattggatg aagatactc                                             19

<210> SEQ ID NO 7
<211> LENGTH: 36
<212> TYPE: DNA
<213> ORGANISM: Artificial Sequence
<220> FEATURE:
<223> OTHER INFORMATION: 5' RACE primer to anneal with poly-C-tailed
      cDNA primer alpha.
<221> NAME/KEY: misc_feature
<222> LOCATION: (0)...(0)
<223> OTHER INFORMATION: n = inosine

<400> SEQUENCE: 7
ggccacgcgt cgactagtac gggnngggnn gggnng                          36

<210> SEQ ID NO 8
<211> LENGTH: 20
<212> TYPE: DNA
<213> ORGANISM: Artificial Sequence
<220> FEATURE:
<223> OTHER INFORMATION: Mi28K primer.  Mismatched oligonucleotide
      containing a mutation of the MiAMP1 coding sequence from amino
      acid Q(position 28) to K.

<400> SEQUENCE: 8
gctatacata aaaagggagg                                            20

<210> SEQ ID NO 9
<211> LENGTH: 20
<212> TYPE: DNA
<213> ORGANISM: Artificial Sequence
<220> FEATURE:
<223> OTHER INFORMATION: Mi39K primer.  Mismatched oligonucleotide
      containing a mutation of the MiAMP1 coding sequence from amino
      acid Q(position 39) to K.

<400> SEQUENCE: 9
tacactggaa aaactgctgc                                            20

<210> SEQ ID NO 10
<211> LENGTH: 24
<212> TYPE: DNA
<213> ORGANISM: Artificial Sequence
<220> FEATURE:
<223> OTHER INFORMATION: Mi46K primer.  Mismatched oligonucleotide
      containing a mutation of the MiAMP1 coding sequence from amino
      acid Q(position 46) to K.

-continued

```
<400> SEQUENCE: 10
gcatccagct ttgttgtaga gagc                                              24

<210> SEQ ID NO 11
<211> LENGTH: 24
<212> TYPE: DNA
<213> ORGANISM: Artificial Sequence
<220> FEATURE:
<223> OTHER INFORMATION: Mi54V primer.  Mismatched oligonucleotide
      containing a mutation of the MiAMP1 coding sequence from amino
      acid H(position 54) to V.

<400> SEQUENCE: 11
ggtgttgcag tgaccaggtt tggg                                              24

<210> SEQ ID NO 12
<211> LENGTH: 24
<212> TYPE: DNA
<213> ORGANISM: Artificial Sequence
<220> FEATURE:
<223> OTHER INFORMATION: Mi54K primer.  Mismatched oligonucleotide
      containing a mutation of the MiAMP1 coding sequence from amino
      acid H(position 54) to K.

<400> SEQUENCE: 12
ggtgttgcaa aaaccaggtt tggg                                              24

<210> SEQ ID NO 13
<211> LENGTH: 31
<212> TYPE: DNA
<213> ORGANISM: Artificial Sequence
<220> FEATURE:
<223> OTHER INFORMATION: Oligonucleotide primer from the 5' coding
      region of MiAMP1 (Mi1 primer).

<400> SEQUENCE: 13
acaccatatg agtgcattta cagtatgagt g                                      31

<210> SEQ ID NO 14
<211> LENGTH: 35
<212> TYPE: DNA
<213> ORGANISM: Artificial Sequence
<220> FEATURE:
<223> OTHER INFORMATION: Oligonucleotide primer from the 3' coding
      region of MiAMP1 (Mi2 primer).

<400> SEQUENCE: 14
gaagagtatc ttcatccaat gctaaggatc cacac                                  35

<210> SEQ ID NO 15
<211> LENGTH: 76
<212> TYPE: PRT
<213> ORGANISM: Artificial Sequence
<220> FEATURE:
<223> OTHER INFORMATION: Mi28K variant.  Variant MiAMP1 protein Mi28K
      containing a Lysine at amino acid 28 (used primer from SEQ ID NO:8
      to produce).

<400> SEQUENCE: 15

Ser Ala Phe Thr Val Trp Ser Gly Pro Gly Cys Asn Asn Arg Ala Glu
 1               5                  10                  15

Arg Tyr Ser Lys Cys Gly Cys Ser Ala Ile His Lys Lys Gly Gly Tyr
            20                  25                  30

Asp Phe Ser Tyr Thr Gly Gln Thr Ala Ala Leu Tyr Asn Gln Ala Gly
        35                  40                  45
```

```
Cys Ser Gly Val Ala His Thr Arg Phe Gly Ser Ser Ala Arg Ala Cys
         50                  55                  60

Asn Pro Phe Gly Trp Lys Ser Ile Phe Ile Gln Cys
 65                  70                  75

<210> SEQ ID NO 16
<211> LENGTH: 76
<212> TYPE: PRT
<213> ORGANISM: Artificial Sequence
<220> FEATURE:
<223> OTHER INFORMATION: Mi39K variant.  Variant MiAMP1 protein Mi39K
      containing a Lysine at amino acid 39 (used primer from SEQ ID NO:9
      to produce).

<400> SEQUENCE: 16

Ser Ala Phe Thr Val Trp Ser Gly Pro Gly Cys Asn Asn Arg Ala Glu
 1               5                  10                  15

Arg Tyr Ser Lys Cys Gly Cys Ser Ala Ile His Gln Lys Gly Gly Tyr
                 20                  25                  30

Asp Phe Ser Tyr Thr Gly Lys Thr Ala Ala Leu Tyr Asn Gln Ala Gly
             35                  40                  45

Cys Ser Gly Val Ala His Thr Arg Phe Gly Ser Ser Ala Arg Ala Cys
         50                  55                  60

Asn Pro Phe Gly Trp Lys Ser Ile Phe Ile Gln Cys
 65                  70                  75

<210> SEQ ID NO 17
<211> LENGTH: 76
<212> TYPE: PRT
<213> ORGANISM: Artificial Sequence
<220> FEATURE:
<223> OTHER INFORMATION: Mi46K variant.  Variant MiAMP1 protein Mi46K
      containing a Lysine at amino acid 46 (used primer from SEQ ID
      NO:10 to produce).

<400> SEQUENCE: 17

Ser Ala Phe Thr Val Trp Ser Gly Pro Gly Cys Asn Asn Arg Ala Glu
 1               5                  10                  15

Arg Tyr Ser Lys Cys Gly Cys Ser Ala Ile His Gln Lys Gly Gly Tyr
                 20                  25                  30

Asp Phe Ser Tyr Thr Gly Gln Thr Ala Ala Leu Tyr Asn Lys Ala Gly
             35                  40                  45

Cys Ser Gly Val Ala His Thr Arg Phe Gly Ser Ser Ala Arg Ala Cys
         50                  55                  60

Asn Pro Phe Gly Trp Lys Ser Ile Phe Ile Gln Cys
 65                  70                  75

<210> SEQ ID NO 18
<211> LENGTH: 76
<212> TYPE: PRT
<213> ORGANISM: Artificial Sequence
<220> FEATURE:
<223> OTHER INFORMATION: Mi54V variant.  Variant MiAMP1 protein Mi54V
      containing a Valine at amino acid 54 (used primer from SEQ ID
      NO:11 to produce).

<400> SEQUENCE: 18

Ser Ala Phe Thr Val Trp Ser Gly Pro Gly Cys Asn Asn Arg Ala Glu
 1               5                  10                  15

Arg Tyr Ser Lys Cys Gly Cys Ser Ala Ile His Gln Lys Gly Gly Tyr
                 20                  25                  30

Asp Phe Ser Tyr Thr Gly Gln Thr Ala Ala Leu Tyr Asn Gln Ala Gly
```

```
                35                  40                  45
Cys Ser Gly Val Ala Val Thr Arg Phe Gly Ser Ala Arg Ala Cys
        50                  55                  60

Asn Pro Phe Gly Trp Lys Ser Ile Phe Ile Gln Cys
65                  70                  75

<210> SEQ ID NO 19
<211> LENGTH: 76
<212> TYPE: PRT
<213> ORGANISM: Artificial Sequence
<220> FEATURE:
<223> OTHER INFORMATION: Mi54K variant.  Variant MiAMP1 protein Mi54K
      containing a Lysine at amino acid 54 (used primer from SEQ ID
      NO:12 to produce).

<400> SEQUENCE: 19

Ser Ala Phe Thr Val Trp Ser Gly Pro Gly Cys Asn Asn Arg Ala Glu
1               5                   10                  15

Arg Tyr Ser Lys Cys Gly Cys Ser Ala Ile His Gln Lys Gly Gly Tyr
            20                  25                  30

Asp Phe Ser Tyr Thr Gly Gln Thr Ala Ala Leu Tyr Asn Gln Ala Gly
                35                  40                  45

Cys Ser Gly Val Ala Lys Thr Arg Phe Gly Ser Ala Arg Ala Cys
        50                  55                  60

Asn Pro Phe Gly Trp Lys Ser Ile Phe Ile Gln Cys
65                  70                  75

<210> SEQ ID NO 20
<211> LENGTH: 76
<212> TYPE: PRT
<213> ORGANISM: Artificial Sequence
<220> FEATURE:
<223> OTHER INFORMATION: Mi46K/54V variant.  Variant MiAMP1 protein
      Mi46K/54V containing a Lysine at amino acid 46 and a Valine at
      amino acid 54.

<400> SEQUENCE: 20

Ser Ala Phe Thr Val Trp Ser Gly Pro Gly Cys Asn Asn Arg Ala Glu
1               5                   10                  15

Arg Tyr Ser Lys Cys Gly Cys Ser Ala Ile His Gln Lys Gly Gly Tyr
            20                  25                  30

Asp Phe Ser Tyr Thr Gly Gln Thr Ala Ala Leu Tyr Asn Lys Ala Gly
                35                  40                  45

Cys Ser Gly Val Ala Val Thr Arg Phe Gly Ser Ala Arg Ala Cys
        50                  55                  60

Asn Pro Phe Gly Trp Lys Ser Ile Phe Ile Gln Cys
65                  70                  75

<210> SEQ ID NO 21
<211> LENGTH: 76
<212> TYPE: PRT
<213> ORGANISM: Artificial Sequence
<220> FEATURE:
<223> OTHER INFORMATION: Mi46K/54K variant.  Variant MiAMP1 protein
      Mi46K/54K containing a Lysine at amino acid 46 and a Lysine at
      amino acid 54.

<400> SEQUENCE: 21

Ser Ala Phe Thr Val Trp Ser Gly Pro Gly Cys Asn Asn Arg Ala Glu
1               5                   10                  15

Arg Tyr Ser Lys Cys Gly Cys Ser Ala Ile His Gln Lys Gly Gly Tyr
            20                  25                  30
```

```
Asp Phe Ser Tyr Thr Gly Gln Thr Ala Ala Leu Tyr Asn Lys Ala Gly
        35                  40                  45

Cys Ser Gly Val Ala Lys Thr Arg Phe Gly Ser Ser Ala Arg Ala Cys
        50                  55                  60

Asn Pro Phe Gly Trp Lys Ser Ile Phe Ile Gln Cys
65                  70                  75
```